United States Patent [19]

Chakravarty et al.

[11] Patent Number: 5,162,340
[45] Date of Patent: Nov. 10, 1992

[54] SUBSTITUTED 1-(2H)-ISOQUINOLINONES BEARING ACIDIC FUNCTIONAL GROUPS AS ANGIOTENSIN II ANTAGONISTS

[75] Inventors: Prasun K. Chakravarty, Edison; William J. Greenlee, Teaneck; Nathan B. Mantlo, Westfield; Arthur A. Patchett; Dooseop Kim, Scotch Plains, all of N.J.

[73] Assignee: Merck & Co., Inc., Rahway, N.J.

[21] Appl. No.: 698,431

[22] Filed: May 10, 1991

[51] Int. Cl.$^5$ .................. A61K 31/47; C07D 217/24
[52] U.S. Cl. .................. 514/309; 514/222.5; 514/237.2; 514/253; 544/2; 544/96; 544/128; 544/363; 546/23; 546/141; 546/142
[58] Field of Search .................. 546/141, 142, 23; 544/128, 363, 2, 96; 514/222.5, 237.2, 253, 309

[56] References Cited

U.S. PATENT DOCUMENTS 4,871,735 10/1989 Heider et al. .................. 546/141

*Primary Examiner*—C. Warren Ivy
*Assistant Examiner*—James H. Turnipseed
*Attorney, Agent, or Firm*—Valerie J. Camara; William H. Nicholson; Joseph F. DiPrima

[57] ABSTRACT

Substituted 1-(2H)-isoquinolinones of the structural formula:

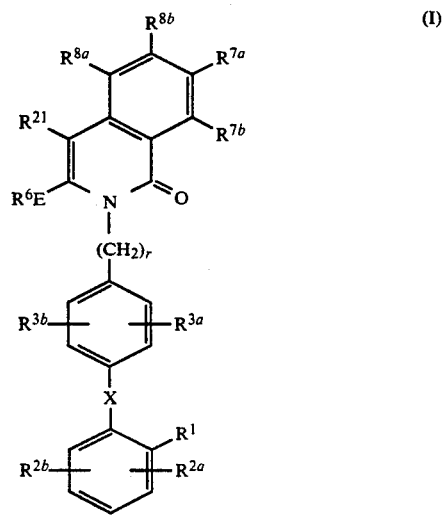

are angiotensin II antagonists which are useful in the treatment of hypertension and congestive heart failure.

6 Claims, No Drawings

SUBSTITUTED 1-(2H)-ISOQUINOLINONES BEARING ACIDIC FUNCTIONAL GROUPS AS ANGIOTENSIN II ANTAGONISTS

SUMMARY OF THE INVENTION

This invention relates to novel compounds of structural formula I which are angiotensin II antagonists useful in the treatment of hypertension, congestive heart failure, and elevated intraocular pressure.

It also relates to processes for preparing the novel compounds; pharmaceutical formulations comprising one or more of the compounds as active ingredient; and, a method of treatment of hypertension, congestive heart failure, and elevated intraocular pressure.

The compounds of this invention also have central nervous sytem (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

In addition, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

BACKGROUND OF THE INVENTION

Renin-angiotensin system (RAS) plays a central role in the regulation of normal blood pressure and seems to be critically involved in hypertension development and maintenance as well as congestive heart failure. Angiotensin II (AII), an octapeptide hormone is produced mainly in the blood during the cleavage of angiotensin I by angiotensin converting enzyme (ACE) localized on the endothelium of blood vessels of lung, kidney, and many other organs, and is the end product of the RAS. AII is a powerful arterial vasoconstricter that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by the partial agonist activity and lack of oral absorption [M. Antonaccio. *Clin. Exp. Hypertens.* A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as A II antagonists. Illustrative of such compounds are those disclosed in U.S. Pat. Nos. 4,207,324; 4,340,598; 4,576,958; 4,582,847; and 4,880,804; in European Patent Applications 028,834; 245,637; 253,310; 291,969; 392,317; 399,731; 403,158; 403,159; 407,342; 411,507; 412,848; and 415,886; and in articles by A. T. Chiu, et al. [*Eur. J. Pharm. Exp. Therap*, 157, 13–21 (1988)] and by P. C. Wong, et al. [*J. Pharm. Exp. Therap*, 247, 1–7 (1988)]. European Patent Applications 028,834 and 253,310 and the above three articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

None of the compounds disclosed in the above identified U.S. Patents, European Applications and articles have the heterobicyclic structure of the compounds of this invention.

DETAILED DESCRIPTION OF THE INVENTION

This invention relates to substituted 1-(2H)-isoquinolinones of the formula I shown below which are angiotensin II antagonists and are primarily useful in the treatment of hypertension.

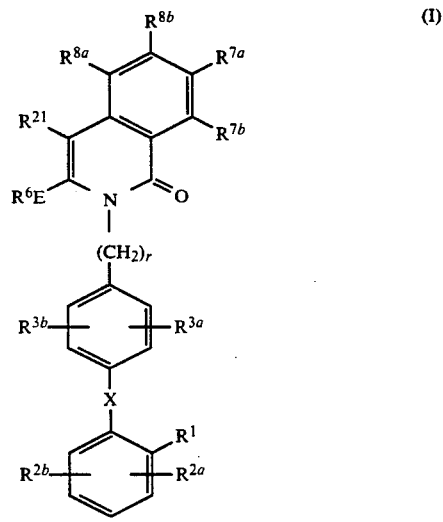

wherein:
R$^1$ is
(a) -SO$_2$N(R$^{22a}$)-OR$^{22a}$,
(b) -SO$_2$NHSO$_2$R$^{22}$,
(c)

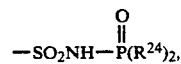

(d)

(e) -SO$_2$NHCN,
(f) -SO$_2$NHCO$_2$R$^{22}$,
(g)

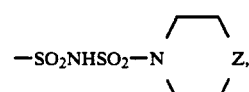

(h) -NHSO$_2$NHSO$_2$R$^{22}$,
(i)

(j) 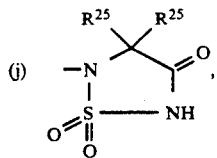

(k) 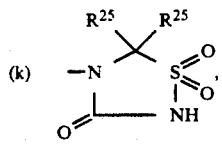

(l) 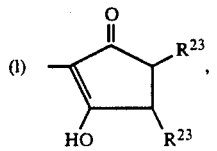

(m) 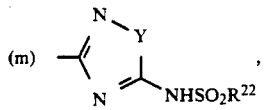

(n) 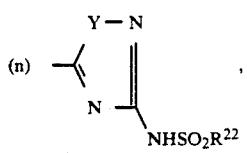

(o) 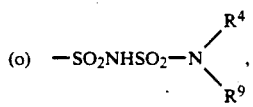

(p) 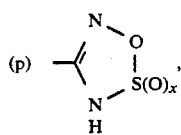

(q) 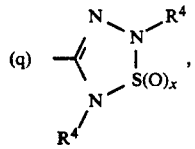

(r) 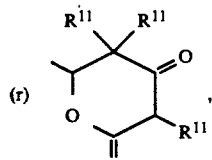

(s) 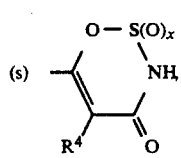

(t) 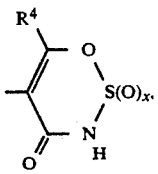

(u) 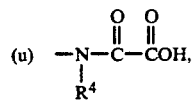

or (v) 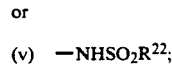

wherein
Y is O or S;
$R^{2a}$ and $R^{2b}$ are each independently
(a) H,
(b) Cl, Br, I, or F,
(c) $NO_2$,
(d) $NH_2$,
(e) $C_1$–$C_4$-alkylamino,
(f) di($C_1$–$C_4$-alkyl)amino,
(g) $SO_2NHR^9$,
(h) $CF_3$,
(i) $C_1$–$C_6$-alkyl,
(j) $C_1$–$C_6$-alkoxy,
(k) $C_1$–$C_6$-alkyl-S-,
(l) $C_2$–$C_6$-alkenyl,
(m) $C_2$–$C_6$-alkynyl;
(n) aryl,
(o) aryl($C_1$–$C_4$-alkyl), or
(p) $C_3$–$C_7$-cycloalkyl;
$R^{3a}$ is
(a) H,
(b) Cl, Br, I, or F,
(c) $C_1$–$C_6$-alkyl,
(d) $C_1$–$C_6$-alkoxy, or
(e) $C_1$–$C_6$-alkoxyalkyl;
$R^{3b}$ is
(a) H,
(b) Cl, Br, I, or F,
(c) $NO_2$,
(d) $C_1$–$C_6$-alkyl,
(e) $C_1$–$C_6$-acyloxy,
(f) $C_3$–$C_7$-cycloalkyl,
(g) $C_1$–$C_6$-alkoxy,
(h) -$NHSO_2R^4$,
(i) hydroxy($C_1$–$C_4$-alkyl),
(j) aryl($C_1$–$C_4$-alkyl),
(k) $C_1$–$C_4$-alkylthio,
(l) $C_1$–$C_4$-alkyl sulfinyl,
(m) $C_1$–$C_4$-alkyl sulfonyl,
(n) $NH_2$,
(o) $C_1$–$C_4$-alkylamino,
(p) di($C_1$–$C_4$-alkyl)amino,
(q) fluoro-$C_1$–$C_4$-alkyl-,
(r) -$SO_2$-$NHR^9$,
(s) aryl,
(t) furyl,
(u) $CF_3$,
(v) $C_2$–$C_6$-alkenyl, or
(w) $C_2$–$C_6$-alkynyl;
wherein aryl is phenyl or naphthyl, or a substituted phenyl or naphthyl with one or two substituents selected from the group consisting of Cl, Br, I, F, N(R$^4$)$_2$, CO$_2$R$^4$, C$_1$-C$_4$-alkyl, C$_1$-C$_4$-alkoxy, NO$_2$, CF$_3$, C$_1$-C$_4$-alkylthio, OH, -SO$_2$NR$^9$R$^{10}$, C$_3$-C$_7$-cycloalkyl, C$_3$-C$_{10}$-alkenyl, or SO(C$_1$-C$_4$-alkyl);

R$^4$ is H, aryl, C$_1$-C$_6$ alkyl, or substituted C$_1$-C$_6$ alkyl in which substituent is aryl or heteroaryl, wherein heteroaryl is an unsubstituted, monosubstituted or disubstituted heteroaromatic 5 or 6 membered ring which contains one to three heteroatoms selected from the group consisting of N, O, and S, and wherein the substituents are members selected from the group consisting of -OH, -SH, C$_1$-C$_4$-alkyl, C$_1$-C$_4$-alkoxy, -CF$_3$, Cl, Br, I, F, and NO$_2$;

R$^{4a}$ is aryl, C$_1$-C$_6$-alkyl or aryl-C$_1$-C$_6$-alkyl;

R$^5$ is H,

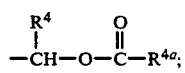

E is a single bond, -NR$^{13}$(CH$_2$)$_s$-, -S(O)$_x$(CH$_2$)$_s$- where x is 0 to 2 and s is 0 to 5, -CH(OH)-, —O—, or CO—;

R$^6$ is
 (a) aryl as defined hereinabove,
 (b) C$_1$-C$_6$-alkyl, C$_2$-C$_5$-alkenyl or C$_2$-C$_5$-alkynyl, or a substituted C$_1$-C$_6$-alkyl, a substituted C$_2$-C$_5$-alkenyl or a substituted C$_2$-C$_5$-alkynyl, in which the substituent is selected from the group consisting of aryl, C$_3$-C$_7$-cycloalkyl, Cl, Br, I, F, CF$_3$, CF$_2$CF$_3$, -NH$_2$, -NH(C$_1$-C$_4$-alkyl), -OR$^4$ -N(C$_1$-C$_4$-alkyl)$_2$, -NH-SO$_2$R$^4$, -COOR$^4$, or -SO$_2$NHR$^9$,
 (c) heteroaryl as defined hereinabove,
 (d) C$_3$-C$_7$-cycloalkyl,
 (e) perfluoro-C$_1$-C$_4$-alkyl, or
 (f) H;

R$^{7a}$, R$^{7b}$, R$^{8a}$ and R$^{8b}$ are independently
 (a) H,
 (b) C$_1$-C$_8$-alkyl or a substituted C$_1$-C$_8$-alkyl with a substituent selected from the group consisting of -OH, -guanidino, C$_1$-C$_4$-alkoxy, -N(R$^4$)$_2$, COOR$^4$, -CON(R$^4$)$_2$, -O- COR$^4$, -aryl, -heteroaryl, -S(O)$_x$-R$^{22}$, -tetrazol-5-yl, -CONHSO$_2$R$^{22}$, -SO$_2$NH-heteroaryl, -SO$_2$NHCOR$^{22}$, -PO(OR$^4$)$_2$, -PO(OR$^4$)R$^9$, -SO$_2$NH-CN, -NR$^{10}$COOR$^{22}$, -(CH$_2$)$_{1-4}$R$^4$, -CO-R$^4$, -CO-heteroaryl, -NR$^4$CONR$^4$R$^{22}$ or -NR$^4$COR$^{22}$,
 (c) -C$_3$-C$_7$-cycloalkyl,
 (d) phenyl-C$_1$-C$_6$-alkyl or naphthyl-C$_1$-C$_6$-alkyl in which the phenyl or naphthyl group is unsubstituted, mono or disubstituted with V or W,
 (e) phenyl or naphthyl, or substituted phenyl or naphthyl in which the substituents are V or W,
 (f) Cl, Br, I, or F,
 (g) -OR$^{22a}$,
 (h) -C$_1$-C$_4$-perfluoroalkyl,
 (i) -S(O)$_x$-R$^{22}$,
 (j) -COOR$^4$,
 (k) -SO$_3$H,
 (l) -NR$^4$R$^{22}$,
 (m) -NR$^{22a}$COR$^{22}$,
 (n) -NR$^{22a}$COOR$^{22}$,
 (o) -SO$_2$NR$^4$R$^9$,
 (p) -NO$_2$,
 (q) -N(R$^{22a}$)SO$_2$R$^{22}$,
 (r) -NR$^{22a}$CONR$^4$R$^{22}$,
 (s)

(t) -NHSO$_2$R$^{22}$,
 (u) -SO$_2$NH-heteroaryl,
 (v) -SO$_2$NHCOR$^{22}$,
 (w) -CONHSO$_2$R$^{22}$,
 (x) PO(OR$^4$)$_2$,
 (y) -PO(OR$^4$)R$^4$,
 (z) -tetrazol-5-yl,
 (aa) -CONH(tetrazol-5-yl),
 (bb) -COR$^{22a}$,
 (cc) -SO$_2$NHCN
 (dd) -NR$^{22a}$SO$_2$NR$^4$R$^{22}$,
 (ee) -NR$^{22a}$SO$_2$OR$^{22}$
 (ff) -CONR$^4$R$^{22}$,
 (gg)

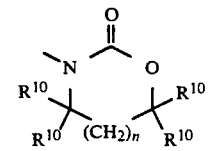

where n=0 or 1, or
 (hh)

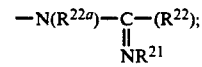

V and W are independently:
 (a) hydrogen,
 (b) C$_1$-C$_5$-alkoxy,
 (c) C$_1$-C$_5$-alkyl,
 (d) hydroxy,
 (e) C$_1$-C$_5$-alkyl-S(O)$_x$-,
 (f) CN,
 (g) NO$_2$,
 (h) N(R$^4$)$_2$,
 (i) CON(R$^4$)$_2$,
 (j) CO$_2$R$^4$,
 (k) COR$^4$,
 (l) CF$_3$,
 (m) Cl, Br, I, or F,
 (n) hydroxy-C$_1$-C$_5$-alkyl,
 (o) C$_1$-C$_5$-alkylthio,
 (p) -SO$_2$NR$^9$R$^{10}$,
 (q) C$_3$-C$_7$-cycloalkyl, or
 (r) C$_2$-C$_{10}$-alkenyl;

R$^9$ is H, C$_1$-C$_5$-alkyl, aryl or arylmethyl;

R$^{10}$ is H, C$_1$-C$_4$-alkyl;

R$^{11}$ is H, C$_1$-C$_6$-alkyl, C$_1$-C$_4$-alkenyl, C$_1$-C$_4$-alkoxy alkyl, or

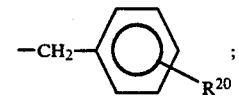

R$^{12}$ is -CN, -NO$_2$, -CF$_3$ or -CO$_2$R$^4$;

R$^{13}$ is H, (C$_1$-C$_4$-alkyl)CO-, C$_1$-C$_6$-alkyl, allyl, C$_3$-C$_6$-cycloalkyl, aryl or arylmethyl;

R$^{14}$ is H, C$_1$-C$_8$-alkyl, C$_1$-C$_8$-perfluoroalkyl, C$_3$-C$_6$-cycloalkyl, aryl or arylmethyl;

$R^{15}$ is H, $C_1$-$C_6$-alkyl;

$R^{16}$ is H, $C_1$-$C_6$-alkyl, $C_3$-$C_6$-cycloalkyl, aryl or arylmethyl;

$R^{17}$ is -$NR^9R^{10}$, -$OR^{10}$, -NHCONH$_2$, -NHCSNH$_2$,

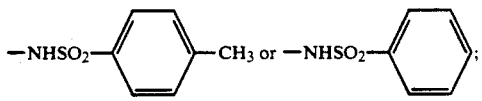

$R^{18}$ and $R^{19}$ are independently $C_1$-$C_4$-alkyl or taken together are -(CH$_2$)$_q$- where q is 2 or 3;

$R^{20}$ is H, -NO$_2$, -NH$_2$, -OH or -OCH$_3$;

$R^{21}$ is
- (a) H,
- (b) Cl, F, Br or I,
- (c) aryl,
- (d) heteroaryl, or
- (e) $C_1$-$C_4$-alkyl or a substituted $C_1$-$C_4$-alkyl with a substituent selected from the group consisting of aryl, heteroaryl, -OH, -NH$_2$, -NH($C_1$-$C_4$-alkyl), -N($C_1$-$C_4$-alkyl)$_2$, -CO$_2$$R^{4a}$, Cl, Br, F, I, or -CF$_3$;

$R^{22}$ is
- (a) aryl,
- (b) heteroaryl,
- (c) $C_3$-$C_7$-cycloalkyl,
- (d) $C_1$-$C_6$-alkyl or a substituted $C_1$-$C_6$alkyl with one or two substituents selected from the group consisting of aryl, heteroaryl, -OH, -SH, $C_1$-$C_4$-alkyl, $C_3$-$C_7$-cycloalkyl, -O($C_1$-$C_4$-alkyl), -S($C_1$-$C_4$-alkyl), -CF$_3$, Cl, Br, F, I, -NO$_2$, -CO$_2$H, CO$_2$-($C_1$-$C_4$-alkyl), -NH$_2$, -NH($C_1$-$C_4$-alkyl), -N($C_1$-$C_4$-alkyl)$_2$, -PO$_3$H$_2$, -PO(OH)(O-$C_1$-$C_4$-alkyl), -PO(OR$^4$)R$^9$, morpholinyl or $C_1$-$C_4$alkylpiperazinyl, or
- (e) perfluoro-$C_1$-$C_4$-alkyl;

$R^{22a}$ is
- (a) hydrogen,
- (b) aryl,
- (c) heteroaryl,
- (d) $C_3$-$C_7$-cycloalkyl,
- (e) $C_1$-$C_6$-alkyl or a substituted $C_1$-$C_6$alkyl with a substituent selected from the group consisting of aryl, heteroaryl, -OH, -SH, $C_1$-$C_4$-alkyl, -O($C_1$-$C_4$-alkyl), -S($C_1$-$C_4$-alkyl), -CF$_3$, Cl, Br, F, I, -NO$_2$, -CO$_2$H, CO$_2$-($C_1$-$C_4$-alkyl), -NH$_2$, -NH($C_1$-$C_4$-alkyl), -N($C_1$-$C_4$-alkyl)$_2$, -PO$_3$H$_2$, -PO(OH)(O-$C_1$-$C_4$-alkyl), -PO(OR$^4$)R$^9$, morpholinyl or $C_1$-$C_4$alkylpiperazinyl, or
- (f) perfluoro-$C_1$-$C_4$-alkyl;

$R^{23}$ is
- (a) H,
- (b) aryl as defined above, or
- (c) $C_1$-$C_6$-alkyl optionally substituted with aryl, F, Cl, Br, -OH, -NH$_2$, -NH($C_1$-$C_4$-alkyl), -N($C_1$-$C_4$-alkyl)$_2$, or CF$_3$;

$R^{24}$ is
- (a) aryl as defined above,
- (b) $C_1$-$C_6$-alkyl optionally substituted with aryl, F, Cl, Br, -OH, -NH$_2$, -NH($C_1$-$C_4$-alkyl), -N($C_1$-$C_4$-alkyl)$_2$, CF$_3$, —COOR$^4$, or CN,
- (c) -OCH(R$^4$)-O-CO-R$^{4a}$, or
- (d) -OH, -O-$C_1$-$C_6$-alkyl wherein alkyl is as defined in (b);

$R^{25}$ is
- (a) H,
- (b) $C_1$-$C_6$-alkyl optionally substituted with aryl, F, Cl, Br, -OH, -NH$_2$, -NH($C_1$-$C_4$-alkyl), -N($C_1$-$C_4$-alkyl)$_2$, CF$_3$, -COOR$^4$, or CN, or
- (c) F, Cl, Br;

X is
- (a) a carbon-carbon single bond,
- (b) -CO-,
- (c) -O-,
- (d) -S-,
- (e)

- (f)

- (g)

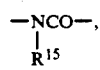

- (h) -OCH$_2$-,
- (i) -CH$_2$O-,
- (j) -SCH$_2$-,
- (k) -CH$_2$S-,
- (l) -NHC(R$^9$)(R$^{10}$),
- (m) -NR$^9$SO$_2$-,
- (n) -SO$_2$NR$^9$-,
- (o) -C(R$^9$)(R$^{10}$)NH-,
- (p) —CH=CH—,
- (q) —CF=CF—,
- (r) —CH=CF—,
- (s) —CF=CH—,
- (t) -CH$_2$CH$_2$-,
- (u) -CF$_2$CF$_2$-, (v) 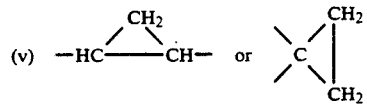

(w) 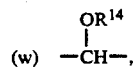

(x) 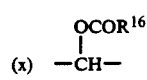

(y) 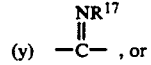, or (z) 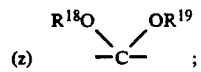 ;

r is 1 or 2, and the pharmaceutically acceptable salts thereof.

The terms "alkyl," "alkenyl," "alkynyl," and the like include both the straight chain and branched chain species of these generic terms wherein the number of carbon atoms in the species permit. Unless otherwise noted, the specific names for these generic terms shall mean the straight chain species. For example, the term "butyl" shall means the normal butyl substituent, n-butyl.

One embodiment of this invention is represented by the compounds of the formula (I) wherein:

$R^1$ is:
(a) $-SO_2N(R^{22a})-OR^{22a}$,
(b) $-SO_2NHSO_2R^{22}$,
(c)

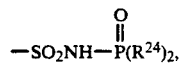

(d) $-SO_2NHCH$,
(e) $-SO_2NHCO_2R^{22}$,
(f)

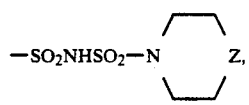

(g) $-SO_2NHSO_2-N(R^4)(R^9)$,
(h) $-NHSO_2NHSO_2R^{22}$, or
(i)

(j)

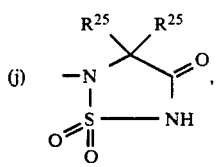

(k)

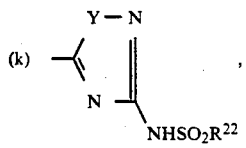

(l)

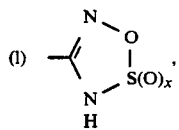

(m)

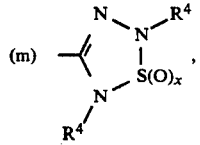

(n)

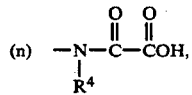

or (o) $-NHSO_2R^{22}$;

X is a single bond;
$R^{2a}$ is H;

$R^{2b}$ is H, F, Cl, $CF_3$, $NO_2$, $C_1-C_6$-alkyl, $C_2-C_6$-alkenyl, $C_2-C_6$-alkynyl, or aryl;

$R^{3a}$ is H;

$R^{3b}$ is H, F, Cl, $CF_3$, $NO_2$, $C_1-C_4$-alkyl, $C_2-C_4$-alkenyl, $C_2-C_4$-alkynyl, $C_5-C_6$-cycloalkyl, $-COOCH_3$, $-COOC_2H_5$, $-SO_2-CH_3$, $NH_2$, $-N(C_1-C_4$-alkyl$)_2$ or $-NH-SO_2CH_3$;

E is a single bond, —O— or —S—;

$R^6$ is
(a) $C_1-C_5$ alkyl or a substituted $C_1-C_5$ alkyl with a substituent selected from the group consisting of $C_3-C_5$-cycloalkyl, Cl, $CF_3$, $CCl_3$, $-O-CH_3$, $-OC_2H_5$, $-S-CH_3$, $-S-C_2H_5$, phenyl, or F;
(b) $C_2-C_5$-alkenyl or $C_2-C_5$-alkynyl; or,
(c) $C_3-C_5$-cycloalkyl;

$R^{7a}$, $R^{7b}$, $R^{8a}$ and $R^{8b}$ are independently
(a) H,
(b) $C_1-C_8$-alkyl or a substituted $C_1-C_8$-alkyl with a COOR, $OCOR^{4a}$, OH, aryl, $-(CH_2)_{1-4}R^4$, $-CO-R^4$, -CO-heteroaryl substituent,
(c) $OR^{22a}$,
(d) $-NO_2$,
(e)

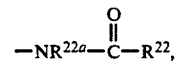

(f) $-CONR^4R^{22}$,
(g)

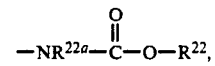

(h) $-NR^4R^{22}$,
(i) Cl, F, or Br,
(j) $-CF_3$,
(k) $-CO_2R^4$,
(l) -CO-aryl,
(m) $-S(O)_x-R^{22}$,
(n) $-SO_2-NR^4R^9$,
(o) $-N(R^{22a})SO_2R^{22}$,
(p) aryl,
(q) heteroaryl,
(r) $-N(R^{22a})CONR^4R^{22}$,
(s) $-N(R^{22a})SO_2N(R^4)R^{22}$, or
(t) $-N(R^{22a})SO_2OR^{22}$;

$R^{21}$ is H, F, or Cl;
X is a single bond;
r is one.

A class of this embodiment is represented by the compound of the formula (I)
$R^1$ is
(a) $-SO_2N(R^{22a})-OR^{22a}$,
(b) $-SO_2NHSO_2R^{22}$,
(c)

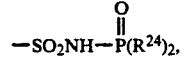

(d) $-SO_2NHCN$,
(e) $-SO_2NHCO_2R^{22}$,
(f)

(g) 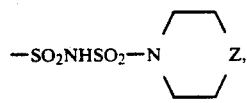

(h) -NHSO₂NHSO₂R²², or (i) 

(j) 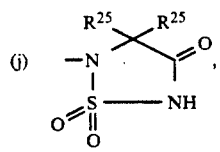

(k) 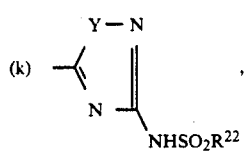

(l) 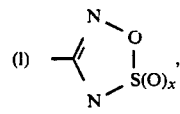

(m) 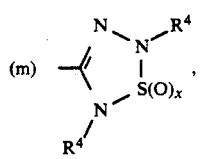

(n) 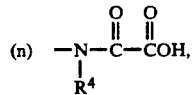

or (o) ;

E is a single bond;

R²ᵇ and R³ᵇ independently are H, -C₁-C₄-alkyl, -C₂-C₄-alkenyl, -C₂-C₄-alkynyl, -Cl, -F, NO₂, or CF₃;

R⁶ is -C₁-C₄-alkyl, -cyclopropyl, -CH₂CH₂CH₂CF₃, CH₂CH₂CF₃, -C₂-C₅-alkenyl, or -cyclopropylmethyl;

R⁷ᵃ, R⁷ᵇ, R⁸ᵃ and R⁸ᵇ are each independently H, -C₁-C₄-alkyl, -NO₂, -NR⁴R²², -OCH₃, -N(R²²ᵃ)-COOR²², -Cl, -CH₂COOR⁴ᵃ, -S(O)ₓ-R²², alkyl, N(R²²ᵃ)CON(R⁴)R²², CH₂OCO(C₁-C₄-alkyl), N(R²²ᵃ)COR²², -F, -CH₂Ph, -CONR⁴R²², or CO₂R⁴.

Illustrating this class are the compounds of the following structural formula (II)

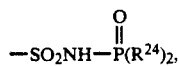

wherein:

R¹ is
(a) -SO₂N(R²²ᵃ)-OR²²ᵃ,
(b) -SO₂NHSO₂R²²,
(c)

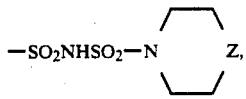

(d) -SO₂NHCN,
(e) -SO₂NHCO₂R²²,
(f)

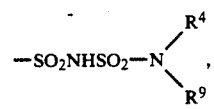

(g)

, (h) -NHSO₂NHSO₂R²², or (i)

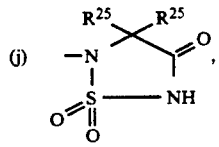

(j)

-continued (k) 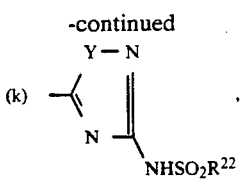

(l) 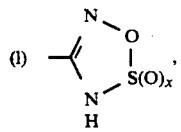

(m) 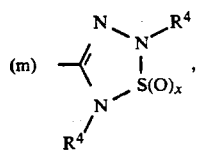

(n) 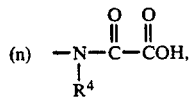

or (o) $-NHSO_2R^{22}$;

$R^4$ is hydrogen or $C_1$–$C_6$alkyl;
$R^6$ is
  (a) $-C_1$–$C_4$alkyl,
  (b) $-CH_2CH_2CH_2CF_3$,
  (c) $-CH_2CH_2CF_3$,
  (d) cyclopropylmethyl, or
  (e) cyclopropyl;
$R^{7a}$ is
  (a) hydrogen,
  (b) $C_1$–$C_4$alkyl,
  (c) $-NR^4R^{22}$,
  (d) $-NR^{22a}CONR^4R^{22}$,
  (e) $-NR^{22a}COR^{22}$, or
  (f) $-NR^{22a}CO_2R^{22}$;
$R^{7b}$ is
  (a) hydrogen
  (b) $C_1$–$C_4$alkyl,
  (c) F, or
  (d) $CO_2R^4$;
$R^{8a}$ is
  (a) hydrogen,
  (b) $C_1$–$C_4$alkyl,
  (c) F;
$R^{8b}$ is
  (a) hydrogen,
  (b) $C_1$–$C_4$alkyl,
  (c) $-CO_2R^4$;
$R^{21}$ is hydrogen or F;
$R^{22}$ is
  (a) phenyl,
  (b) 4-F-phenyl,
  (c) 4-CF$_3$-phenyl, or
  (d) $C_1$–$C_6$alkyl; and
$R^{22a}$ is
  (a) hydrogen,
  (b) $C_1$–$C_6$alkyl, or
  (c) benzyl.

Exemplifying this subclass are the following compounds of the Formula II (wherein $R^{7a}$, $R^{7b}$, $R^{8a}$, $R^{8b}$ and $R^{21}$ are hydrogen) shown in Table A:

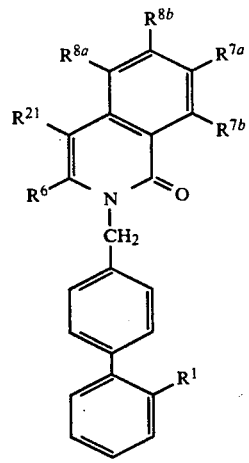

(II)

TABLE A

| Compound No. | $R^1$ | $R^6$ |
|---|---|---|
| A1 | $-SO_2NHOH$ | Pr |
| A2 | $-SO_2NHSO_2Ph$ | Pr |
| A3 | $-SO_2NHSO_2Me$ | Bu |
| A4 | $-SO_2NHSO_2-iPr$ | Pr |
| A5 | (methyl-oxathiadiazole dioxide) | Bu |
| A6 | (methyl-N-Ph-thiadiazole oxide) | Bu |
| A7 | $-NH-C(O)-CO_2H$ | Bu |
| A8 | $-SO_2NHSO_2-iPr$ | Bu |
| A9 | $-SO_2NHP(O)(O-CH_2Ph)_2$ | Bu |
| A10 | (cyclic sulfamide with ketone) | Bu |
| A11 | (N-O heterocycle) $-NHSO_2Ph$ | Bu |
| A12 | (methyl-oxathiadiazole dioxide) | Bu |

TABLE A-continued

| Compound No. | R¹ | R⁶ |
|---|---|---|
| A13 | —NHSO₂—(thiophene-S) | Bu |
| A14 | —NHSO₂—(2,4-difluorophenyl) | Pr |
| A15 | —SO₂NHCO₂Et | Pr |
| A16 | —SO₂NHCO₂i-Pr | Pr |
| A17 | —SO₂NHPO(OEt)₂ | Pr |

The compounds of Formula (I) can be synthesized using the reactions and techniques described below. The reaction are performed in a solvent appropriate to the reagents and materials employed and suitable for the transformation being effective. It is understood by those skilled in the art of organic synthesis that the functionality present on the heterocycle and other parts of the structure should be consistent with the chemical transformations proposed. Depending upon the reactions and techniques employed, this may involve changing the order of the synthetic steps, the use of required protecting groups followed by deprotection, and, depending upon the particular pyrimidinone fused heterocycle being formed, the use of different strategies may be employed regarding the cyclization steps and the particular starting materials utilized.

ABBREVIATIONS USED IN REACTION SCHEMES

Reagents:
| | |
|---|---|
| NBS | N-bromosuccinimide |
| AIBN | azo(bis)isobutyronitrile |
| DDQ | dichlorodicyanoquinone |
| Ac₂O | acetic anhydride |
| TEA | triethylamine |
| DMAP | 4-dimethylaminopyridine |
| PPh₃ | triphenylphosphine |
| TFA | trifluoroacetic acid |
| TMS-Cl | trimethylsilyl chloride |
| Im | imidazole |
| AcSK | potassium thioacetate |
| p-TsOH | p-toluenesulfonic acid |

Solvents:
| | |
|---|---|
| Et₂O | diethyl ether |
| DMF | dimethylformamide |
| HOAc (AcOH) | acetic acid |
| EtOAc (EtAc) | ethyl acetate |
| Hex | hexane |
| THF | tetrahydrofuran |
| DMSO | dimethylsulfoxide |
| MeOH | methanol |
| iPrOH | isopropanol |
| DBU | 1,8-diazabicyclo-[5.4.0]undec-7-ene |
| Me₃SnCl | trimethylstannyl chloride |

Others:
| | |
|---|---|
| rt | room temperature |
| TBDMS | t-butyldimethylsilyl |
| OTf | OSO₂CF₃ |
| OTs | OS)₂-(4-methyl)phenyl |
| OMs | OSO₂CH₃ |
| Ph | phenyl |
| FAB-MS (FABMS) | Fast atom bombardment mass spectroscopy |
| NOE | Nuclear Overhauser Effect |
| SiO₂ | silica gel |
| trityl | triphenylmethyl. |
| s.b. | single bond |

Compounds of Formula (I) may be prepared via intermediate 4 by alkylation of the anion of 1(2H) isoquinolinone 2 with alkylating agent 3 (Scheme 1). Alternatively, the isoquinolinone may be converted to a silyl imine and then regioselectively alkylated on nitrogen by treatment with the alkylating agent in the presence of fluoride ion. Deprotection of the R¹ protecting group of intermediate product 4 will give rise to compounds of Formula I. Alternatively, if R¹ is nitrile and a tetrazole is desired, trimethyltin azide will convert the intermediate 4 to 1 where R¹ is tetrazole.

SCHEME 1

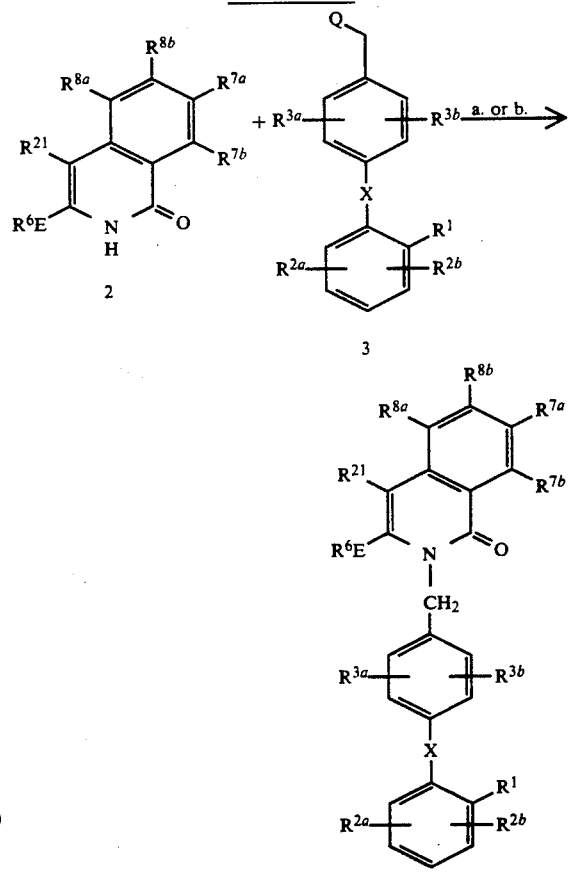

(4 where r = 1 and R¹ is protected)
(I where r = 1 and R¹ is unprotected)

Q = halogen, —O-tosyl or —O-mesyl
a. NaH, DMF
b. (i) [(CH₃)₃Si]₂NH or (CH₃)₃SiCl/Et₃N (ii) 3, F⁻

Isoquinolinones 2 and 2,3-disubstituted isoquinolinones 4 may be prepared from isocoumarins 5 (Scheme 2). There are many synthetic approaches available to isocoumarins. [Compendium of Heterocyclic Chemistry] Treatment of an isocoumarin with ammonia will give rise to the isoquinolinones 2. Treatment of the isocoumarin with an alkyl amine 6 will give rise to the 2-substituted isoquinolinone 4. Both 2 and 4 may then be transformed into compounds of Formula I as shown in Scheme 1.

SCHEME 2

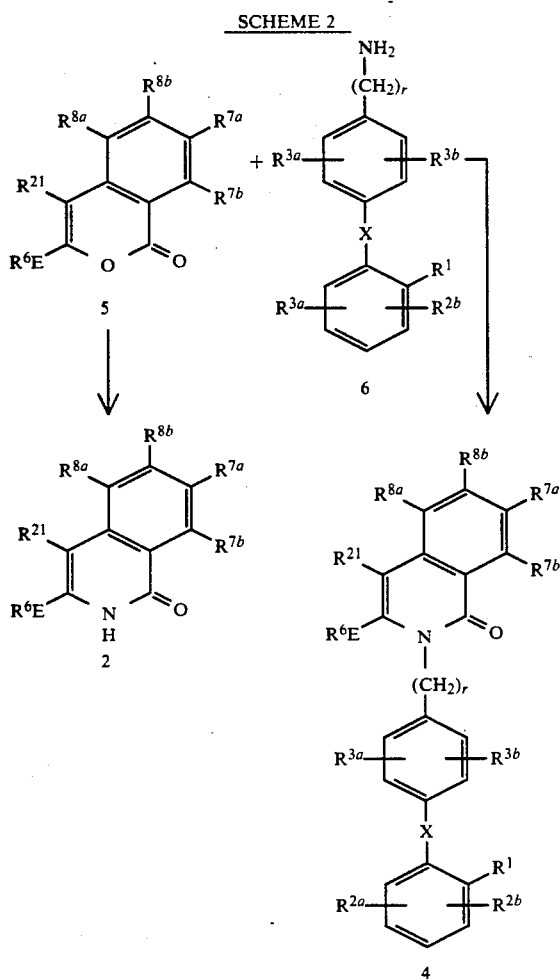

One of the most useful methods of preparing 1(2H)-isoquinolinones is from homophthalic anhydrides 7 (Scheme 3). [R. B. Tirodkar, R. N. Usgaonkar. *Indian J. Chemistry*, 1060, 1972] Acylation of 7 under basic conditions with anhydrides gives rise to intermediate 4-acylisochroman-1,3-diones 8. In a similar fashion the diacid 9 may also be converted to 8. Treatment of 8 with ammonia will give rise to 1(2H)-isoquinolinones 2. Alternatively, acid treatment results in decarboxylation and formation of an isocoumarin 5. Both 2 and 5 may in turn be converted to compounds of Formula I by following Schemes 1 and 2, respectively.

SCHEME 3

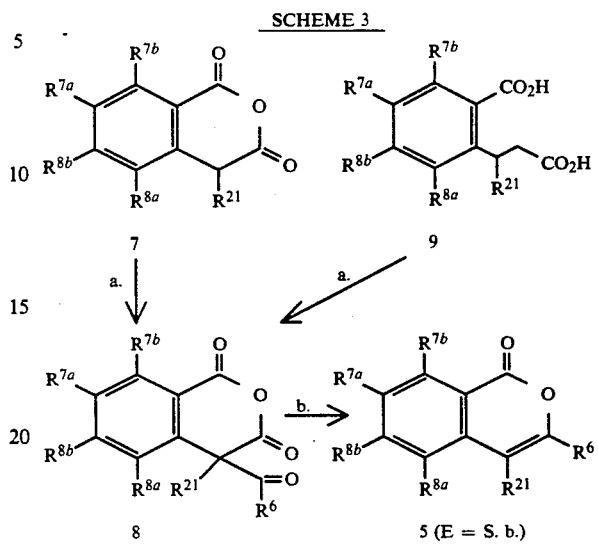

a. $(R^6CO)_2O$, py
b. $H_2SO_4$, 95° C.

There are several other direct routes to 1(2H)-isoquinolinones 2 shown in Scheme 4. Treatment of 10 with an alkyl metal enolate and irradiation will give rise directly to a 1(2H)-isoquinolinone 2. [R. Beugelmans, M. Bois-Coussy. *Synthesis*. 729, 1981] Similarly, o-iodo benzamides 11 may be alkylated with copper acetylides in pyridine to give intermediate acetylide 12. These may be cyclized to give 2 under palladium catalysis in the presence of sodium hydride in THF [A. Nagarajan, T. R. Balasubramanian, *Ind. J. Chem.* 67, 1989]. 2-Substituted indanones 13 may be rearranged to intermediate 2-alkyl-N-hydroxy-1(2H)-isoquinolinones 14 by treatment with an alkyl nitrite in the presence of acid. Reduction of 14 with, for example, iodine and red phosphorous will give 2. [E. J. Moriconi, F. J. Creegan. *J. Org. Chem.* 31, 2090, 1966] 2-N-Methyl benzamides 15 may be converted to the intermediate dilithio species with n-butyl lithium. Addition of an alkyl nitrile followed by acid gives rise to 2 [G. S. Poindexter. *J. Org. Chem.* 3787, 1982]. The 1-(2H)-isoquinolinones may be converted to compounds of formula I by following the chemistry described in Scheme 1.

SCHEME 4

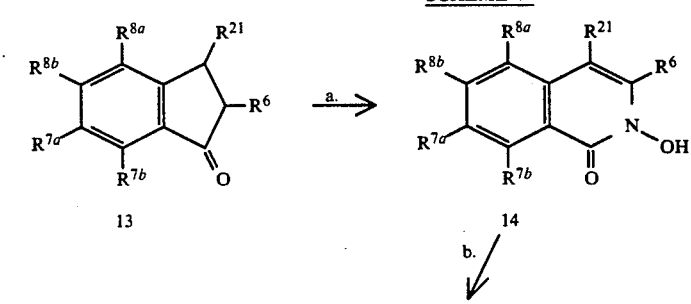

SCHEME 4

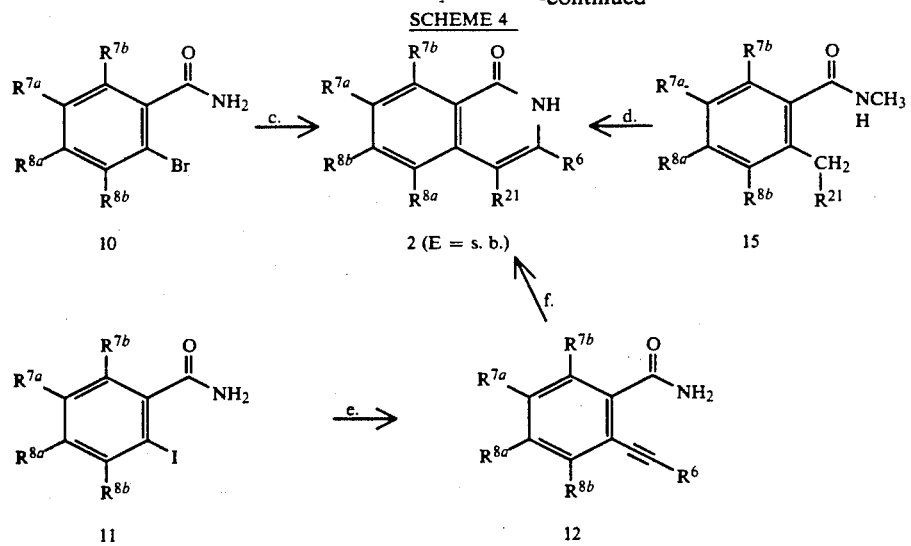

a. (i) nBuNO₂, H₂SO₄ (ii) MeOH, Δ
b. I₂, P
c. $\overset{O^-}{\underset{R^6}{\diagup\!\!\!\diagdown}}$, hν
d. (i) BuLi, (ii) R⁶CN, (iii) H⁺
e. Cu—C≡C—R⁶, pyridine
f. PdCl₂, CH₃CN, NaH, THF.

Two alternative routes directly to 2,3-disubstituted isoquinolinones 19 may be available as shown in Scheme 5. Irradiation of N-vinyl benzamides 16 in methanol followed by oxidation by treatment with iodine will give rise to 2,3-disubstituted isoquinolinones 19. [A. Couture, P. Grandclaudin. *Synthesis*, 576, 1985] Alternatively, 2-methyl benzamides 17 may be dilithiated with n-butyl lithium and treated with an amide 18 to give the 2,3-disubstituted isoquinolinone 19. Compound 19 may then be elaborated to give compounds of Formula I.

SCHEME 5

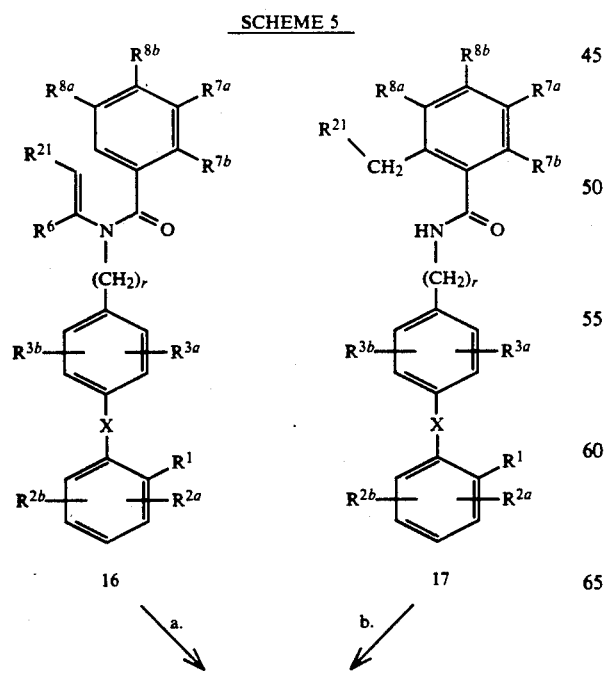

a. hν, argon, CH₃OH, I₂
b. (i) BuLi, (ii) R⁶CON(CH₃)₂ (18).

The benzyl halides (3) including the more preferred alkylating agents (21a, 21b and 21c, Scheme 6) can be prepared as described in European Patent Applications 253,310 and 291,969 and the references cited therein. However, a preferred method to prepare the biphenyl precursors 22a, 22b and 22b, using Ni(O) or Pd(O) catalyzed cross-coupling reaction [E. Negishi, T. Takahashi, and A. O. King, *Org. Synthesis*, 66, 67 (1987)], is outlined in Scheme 6. As shown in Scheme 6, treatment of 4-bromotoluene (23) with t-BuLi, followed by the addition of a solution of ZnCl$_2$, produces the organo-zinc compound (24). Compound (24) is then coupled with 25a or 25b in the presence of Ni(PPh$_3$)$_2$Cl$_2$ catalyst to produce the desired biphenyl compound 22a or 22b (PPh$_3$=triphenylphosphine). Similarily, 1-iodo-2-nitrobenzene (25c) is coupled with organo-zinc compound 24 in the presence of Pd(PPh$_3$)$_4$ catalyst [prepared by treating Cl$_2$Pd(PPh$_3$)$_2$ with (i-Bu)$_2$AlH (2 equiv.)] to give the biphenyl compound 22c. These precursors, 22a, 22b and 22c, are then transformed into halomethyl-biphenyl derivatives 21a, 21b and 21c, respectively, according to procedures described in European Patent Applications 253,310 and 291,969.

SCHEME 6

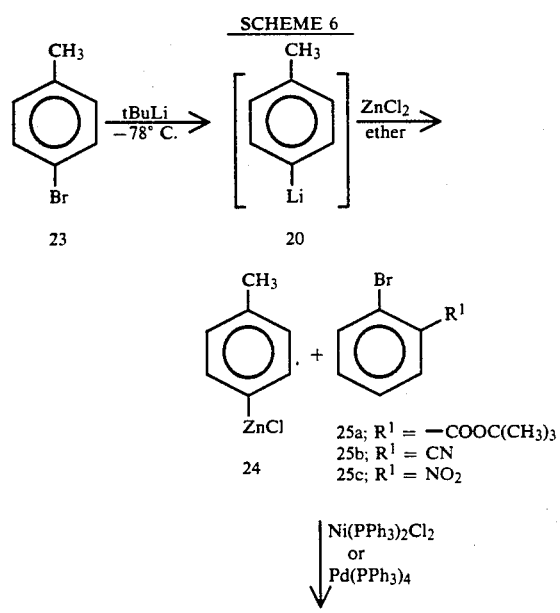

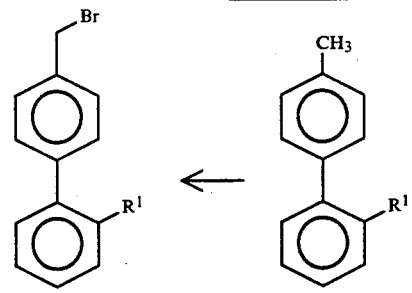

21a; R$^1$ = —COOC(CH$_3$)$_3$    22a; R$^1$ = —COOC(CH$_3$)$_3$
21b; R$^1$ = —CN                    22b; R$^1$ = CN
21c; R$^1$ = —NO$_2$                22c; R$^1$ = NO$_2$

When there is additional substitution on the second phenyl ring (R$^{2a}$, R$^{2b}$=hydrogen) the preferred method to prepare the biphenyl precursors 22d and 22e, using the Pd(0) catalyzed cross-coupling reaction [J. K. Stille, Angew, Chem. Int. Ed. Engl., 25, 508 (1986)], is outlined in reation Scheme 7. As shown in Scheme 7, p-tolyl-trimethyltin (26) is coupled with 25d or 25e in refluxing toluene in the presence of 5 mole % of Pd(PPh$_3$)$_4$ to produce the desired biphenyl compounds 22d and 22e. Table I illustrates the synthetic utility of this protocol. Compounds 22d (R$^2$=NO$_2$) and 22e (R$^2$=NO$_2$) could be converted to their respective chlorides by catalytic hydrogenation, diazotization and treatment with copper (I) chloride. The biphenyl fluorides which could not be obtained by direct coupling to a fluoro arylbromide were prepared from 22d (R$^2$=NO$_2$) and 22e (R$^2$=NO$_2$) via reduction, formation of the diazonium tetrafluoroborate salt and thermal decomposition. These precursors 22d (R$^2$=NO$_2$ of F or Cl) and 22e (R$^2$=NO$_2$ or F or Cl) are then transformed into the halomethyl biphenyl derivatives 21d and 21e, respectively according to the procedures described in European Patent Applications 253,310 and 292,969.

Biphenyl Synthesis Table I

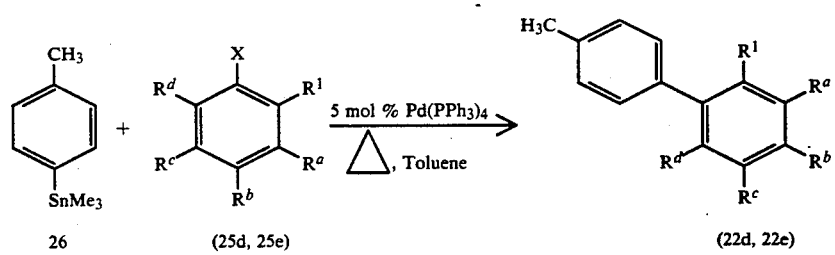

| X | R$^1$ | R$^a$ | R$^b$ | R$^c$ | R$^d$ | Product (R$^a$) | Rf (solvent) | Yield |
|---|---|---|---|---|---|---|---|---|
| Br | CO$_2$Me | NO$_2$ | H | H | H | 22d (3'-nitro) | 0.35 (15:1 Hex/EtOAc) | 71% |
| Br | CN | H | NO$_2$ | H | H | 22e (4'-nitro) | 0.62 (2 × 6:1 Hex/EtOAc) | 74% |
| Br | CO$_2$Me | H | F | H | H | 22d (4'-fluoro) | 0.43 (15:1 Hex/EtOAc) | 83% |
| Cl | CO$_2$Me | H | H | NO$_2$ | H | 22d (5'-nitro) | 0.22 (15:1 Hex/EtOAc) | 70% |
| Br | CO$_2$Me | H | H | H | NO$_2$ | 22d (6'-nitro) | 0.24 (15:1 Hex/EtOAc) | 79% |
| Br | CN | H | F | H | H | 22e (4'-fluoro) | 0.44 (15:1 Hex/EtOAc) | 64% |
| Cl | CN | H | H | F | H | 22e (5'-fluoro) | 0.40 (15:1 Hex/EtOAc) | 62% |

SCHEME 7

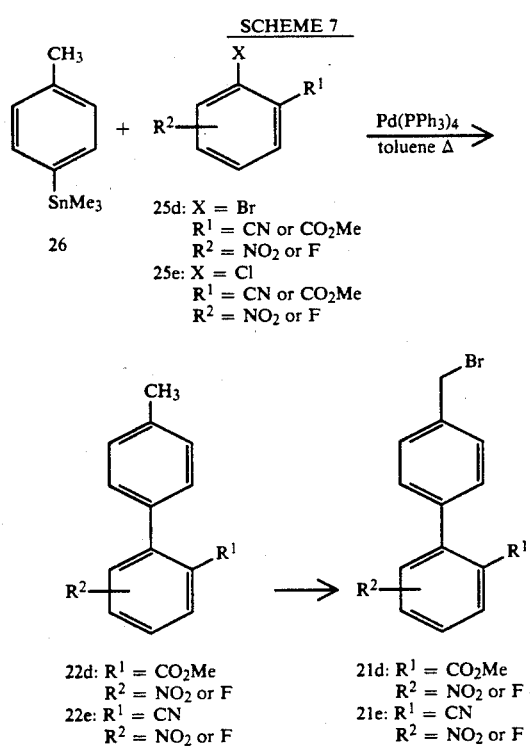

Compounds of formula I where $R^1$ is

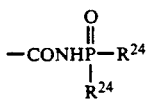

may be prepared from the corresponding carboxylic acid derivatives (I) as outlined in Scheme 8. The carboxylic acid (I), obtained as described in Scheme 1, can be converted into the corresponding amide by treatment with carbonyldiimidazole and then with ammonia. The resulting amide then can be treated with sodium hydride or n-butyllithium in THF at $-20°$ C. followed by an appropriately substituted phosphonyl or phosphinyl halide to form the desired compounds (27).

SCHEME 8

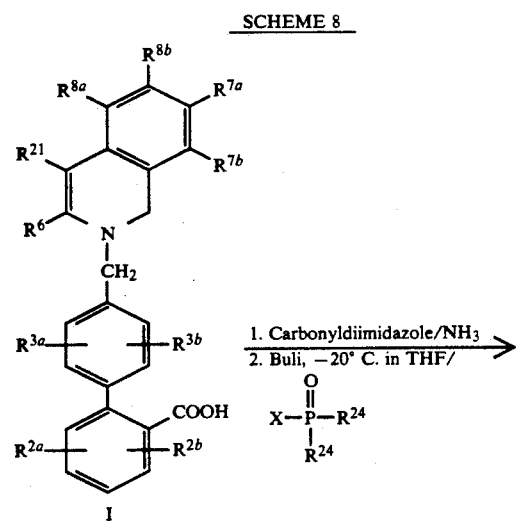

-continued
SCHEME 8

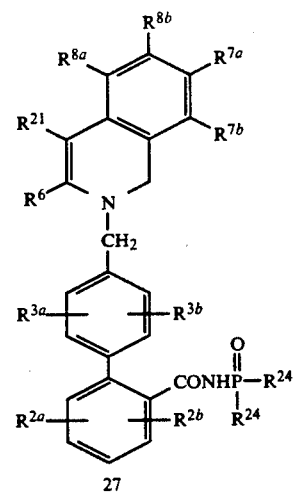

The biaryl sulfonamides (32) and (37), precursors for the alkylating agent 33, can be prepared from appropriate aryl-organotin precursors using palladium(0) catalyzed cross-coupling reactions [J. K. Stille, *Pure Appl. Chem.*, 57, 1771 (1985); T. R. Baiely, *Tetra Lett.*, 27, 4407 (1986); D. A. Widdowson and Y. Z. Zhang, *Tetrahedron*, 42, 2111 (1986)], as outlined in Schemes 9 and 10. The organotin compound (26) [S. M. Moerlein, *J. Organometallic Chem.*, 319, 29 (1987)], obtained from the aromatic precursors (28 or 29), may be coupled with aryl sulfonamide (31) using $Pd(PPh_3)_4$ or $(PPh_3)_2PdCl_2$ as catalysts to give biaryl sulfonamide 32. Similarly, the biphenylmethyl bromide (33) may be alternatively prepared from the appropriate organotin precursor (36) using the Pd(0) catalyzed cross-coupling reaction as outlined in Scheme 10.

SCHEME 9

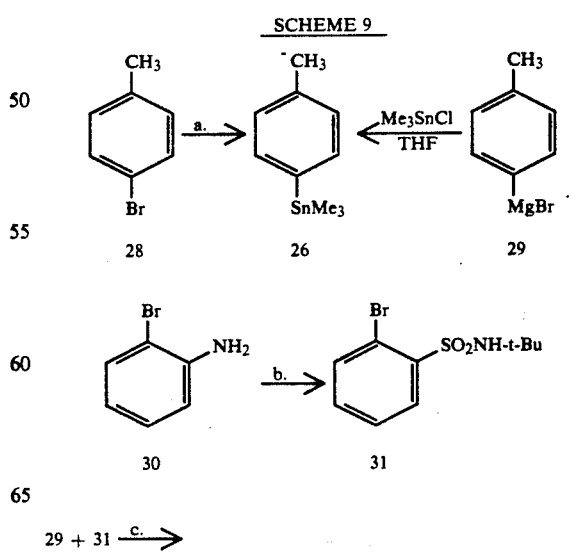

-continued
SCHEME 9

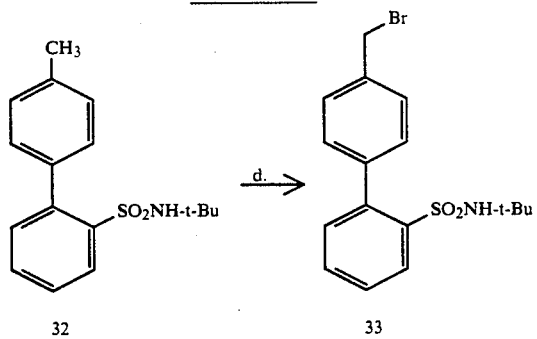

32 → 33 a. i) t-BuLi/ether, −78° C. ii) Me₃SnCl
b. i) NaNO₂/HCl ii) SO₂, CuCl₂ (iii) t-butylamine
c. Pd(PPh₃)₄, Toluene or (PPh₃)₂PdCl₂, DMF, Heat
d. NBS/CCl₄, AIBN, Reflux

SCHEME 10

34 → 35 → 36

31

37

33 a. t-BuMe₂Si—Cl/Imidazole, DMF
b. t-BuLi, −78° C., Me₃SnCl
c. Tetrabutylammonium fluoride
d. CBr₄/Ph₃P.

Compounds of formula I where $R^1$ is $-SO_2NHSO_2R^{22}$ may be prepared from the key sulfonamide intermediate 38 as outlined in Scheme 11. The intermediate 38 may be prepared by the alkylation of appropriate heterocycles with the alkylating agent 33 as outlined in Scheme 1. Treatment of 38 with trifluoroacetic acid followed by acylation of the resulting sulfonamide 39 with appropriate sulfonyl chlorides may produce the desired compounds (40).

SCHEME 11

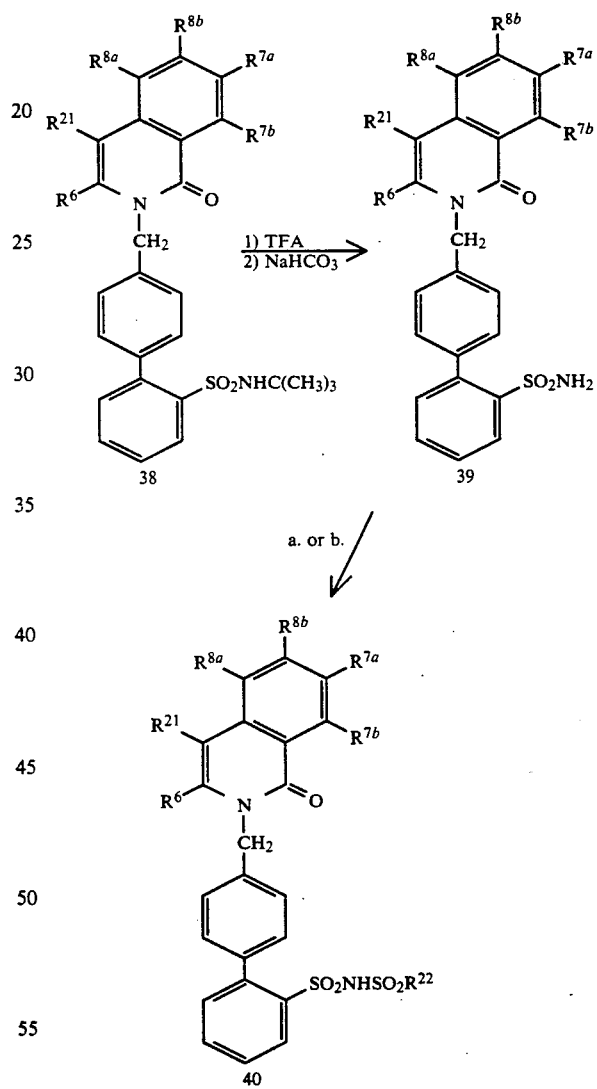

a. i) NaH/THF or DMF (ii) $R^{22}SO_2Cl$
b. $R^{22}SO_2Cl$, DBU, THF

Compounds of Formula (I) wherein $R^1$ is $-SO_2NH-CO_2R^{22}$ may be prepared by reacting an appropriate chloroformate with the sulfonamide (39) in pyridine or in the presence of DBU in THF to afford the desired compound (41), as outlined in Scheme 12.

SCHEME 12

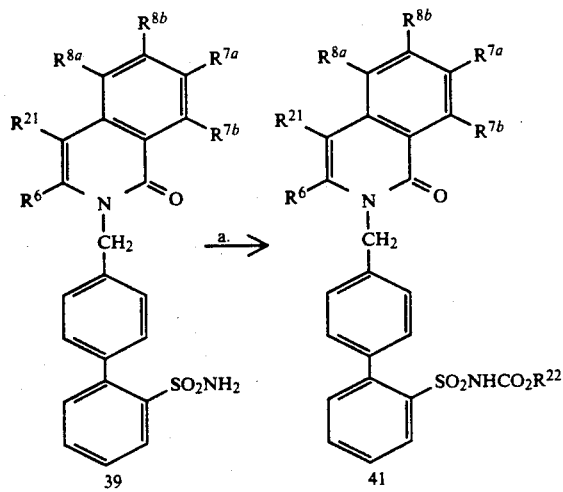

a. R²²OCCl, pyridine or DBU, THF

Compounds of Formula (I) wherein R¹ is

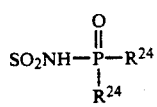

may be prepared by treating sulfonamide (39) with n-butyllithium in THF followed by the treatment of the resulting anion with an appropriately substituted phosphonyl or phosphinyl halide to form the desired compounds (42). (Scheme 13)

SCHEME 13

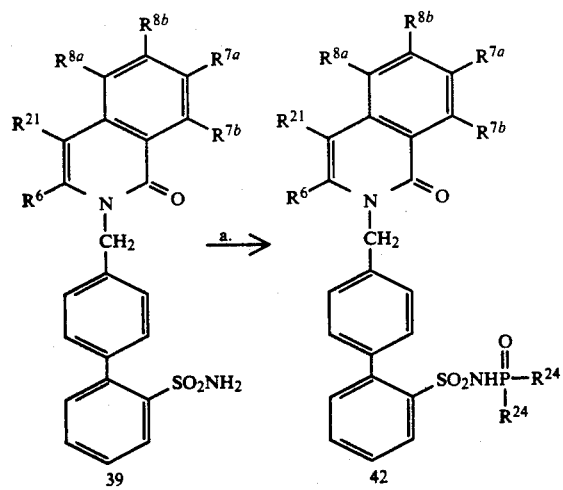

a. BuLi, −20° C. in THF/X—PR²⁴
                               ‖
                               O
                               R²⁴

Compounds of Formula (I) wherein R¹ is SO₂N-HSO₂N(R⁴)(R⁹) or

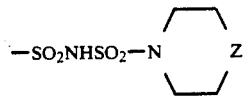

may also be prepared from sulfonamide (39) as outlined in Scheme 14. Treatment of 39 with n-butyllithium in THF at −25° C. and then with an appropriate sulfamoyl halide may produce the desired product (43) or (44).

SCHEME 14

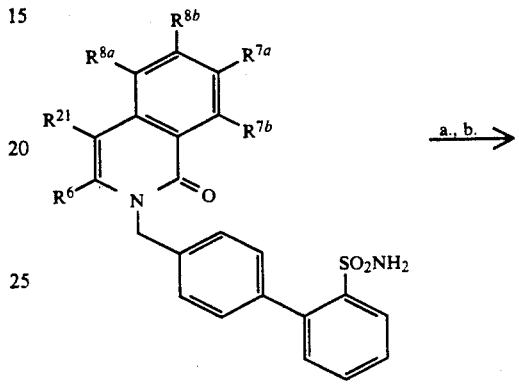

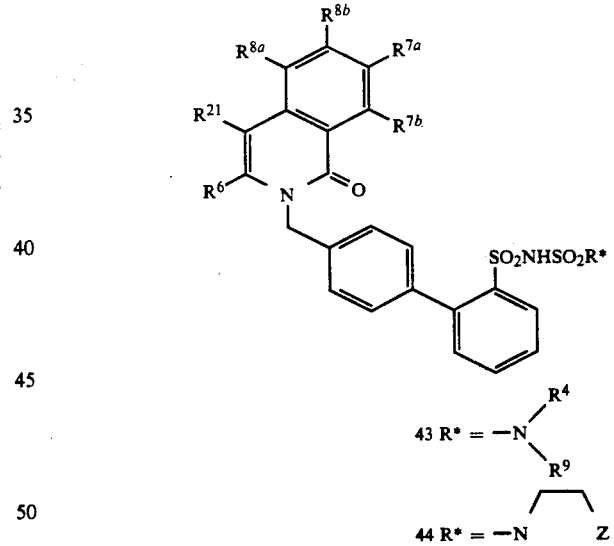

a. nBuLi, −25° C. in THF
b. R*—SO₂Cl

Compounds of Formula (I) wherein R¹ is -NHSO₂N-HSO₂R²² or

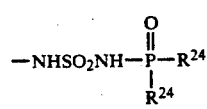

may be prepared from arylamine (46) as outlined in Scheme 15. The arylamine (46) obtained from the corresponding nitro compound 45 can be treated with t-butylsulfamoyl chloride to afford the protected amino sulfonamide (47). The amino sulfonamide (48) obtained after removal of the t-butyl protecting group may then be reacted with an appropriate acylating agent in the presence of a base such as pyridine or DBU in an organic solvent such as THF or DMF to form the desired products (49a) or (49b).

Compounds of the Formula (I) wherein $R^1$ is -NHSO$_2$R$^{22}$ may be prepared by the reaction of an appropriate sulfonyl halide (R$^{22}$SO$_2$Cl) or sulfonyl imidazole derivative with the aryl amine 46 in the presence of an appropriate base such as pyridine, triethylamine or DBU.

derivative (50) or cyano precursor (22b) as outlined in Schemes 16 and 17, respectively utilizing procedures described in U.S. Pat. No. 4,910,019. The cyano derivatives (50), obtained as described in Scheme 1, can be converted into the corresponding amidoxime (51) by treatment with hydroxylamine hydrochloride and sodium methoxide in an organic solvent, such as methanol or DMSO. The amidoxime (51) then can be treated with base and thionyl chloride in an aprotic solvent to form the desired 1,2,3,5-oxathiadiazole-2-oxide (52). Similarly, the oxathiadiazole-2,2-dioxide 52a can be prepared by treatment of amidoxime 51 with a base and sulfuryl chloride. As shown in Scheme 17, the cyano precursor (22b) may be converted into the desired 1,2,3,5-oxathiadiazole (54) which is then protected with the trityl group prior to the formation of the desired benzyl halide (55). The protecting group is removed subsequent to the alkylation of heterocycle (1) to give the desired product (52).

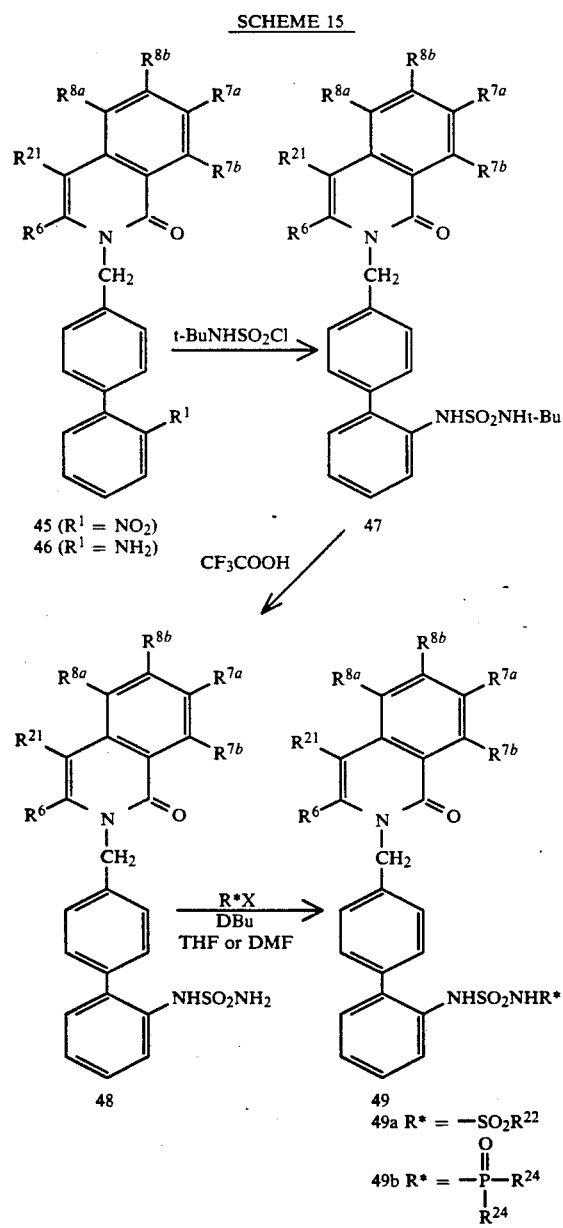

SCHEME 15

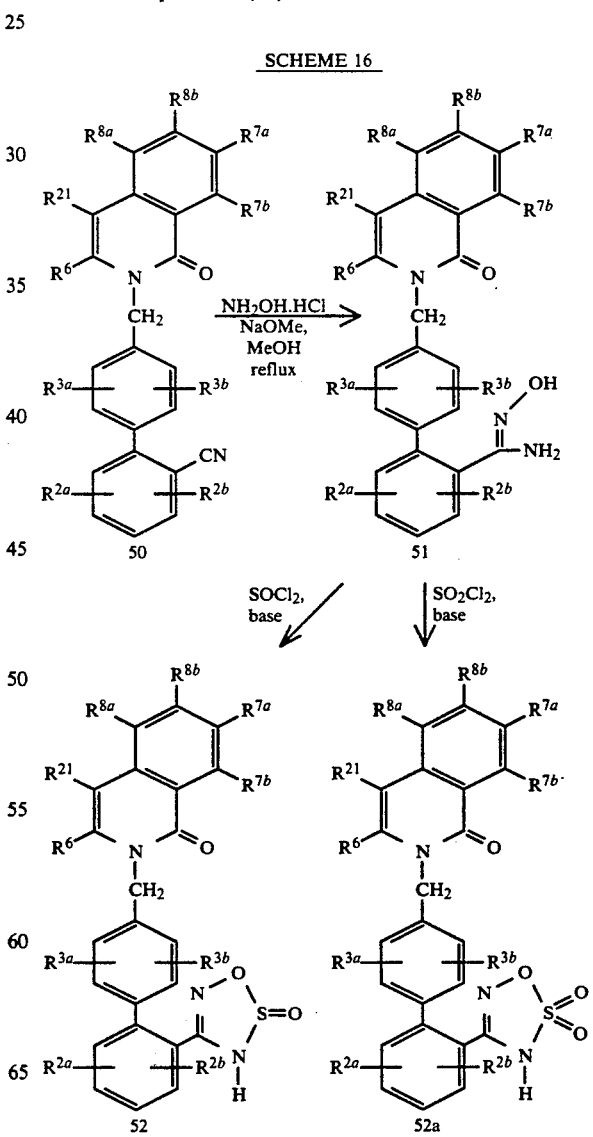

SCHEME 16

Compounds of Formula (I) and the benzyl halides of the formula (55) wherein $R^1$ is 1,2,3,5-oxathiadiazole-2-oxide may be prepared from the corresponding cyano

SCHEME 17

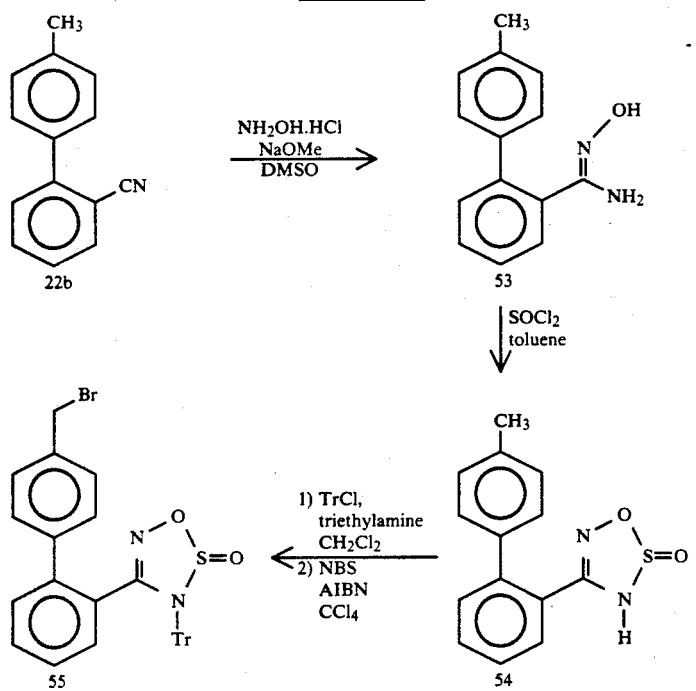

Compounds of Formula (I) and the benzyl halides of the formula (3) wherein $R^1$ is 1,2,3,5-thiatriazole-1-oxide may be prepared from the corresponding precursors 56 or 61 as outlined in Schemes 18 and 19, respectively. Intermediate 61 may be prepared from the biphenyl 22a according to the scheme illustrated (see procedures in U.S. Pat. No. 4,870,186). Intermediates (57) and (62) can be treated with $SOCl_2$ (see procedures in: *Ber. Deutsch. Chem. Ges.* 1971, 104 pp 639) to give intermediates, (58) and (63). Bromination of the N-protected compounds (58) and (63) provides intermediates 60 and 64 respectively. After alkylation with an appropriate heterocycle, the trityl group of the intermediate derived from 60 is removed with protic acid and the cyanoethyl group of the intermediate derived from 64 is removed upon treatment with hydroxide. Alternatively, (60) and (64) may be prepared as shown in Scheme 20 and 21. Treatment of (65) with $SOCl_2$ (see procedures in: *Ber. Deutsch. Chem. Ges.* 1971, 104 pp 639) provides (66), which under mild hydrolytic conditions provides (58). The conversion of (58) to (60) is as described for Scheme 18. Alkylation of the trityl protected analog (67) by treatment with a base such as NaH and an alkyl halide would provide (59), which then may be converted to (64) as previously described.

SCHEME 18

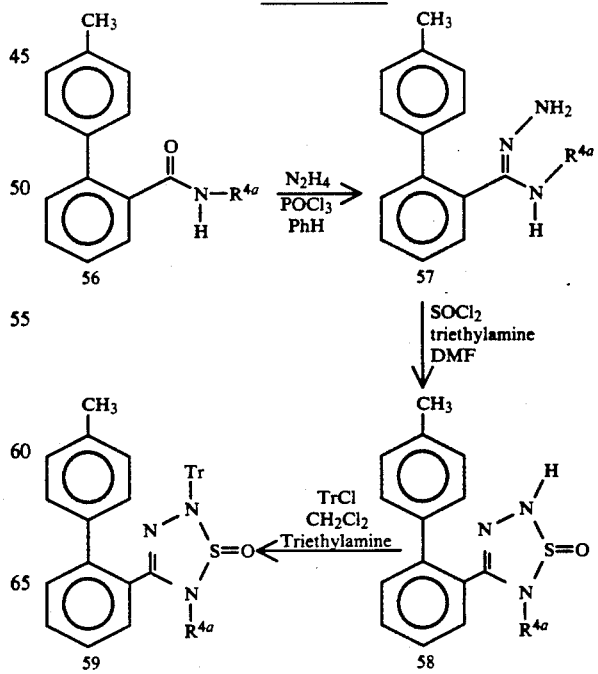

5,162,340
SCHEME 18 -continued
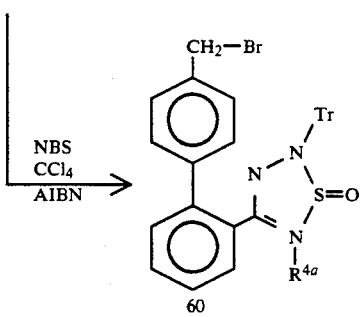
SCHEME 20
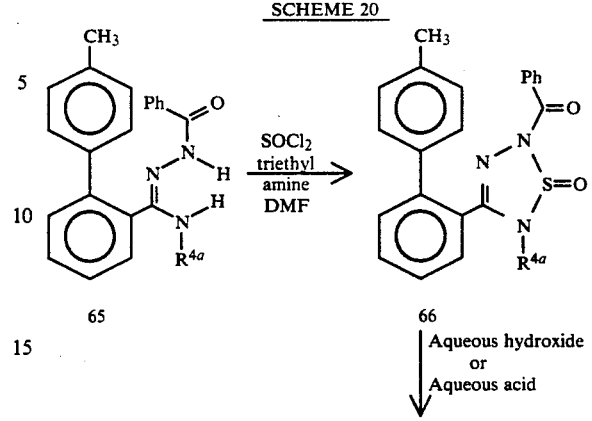
SCHEME 19
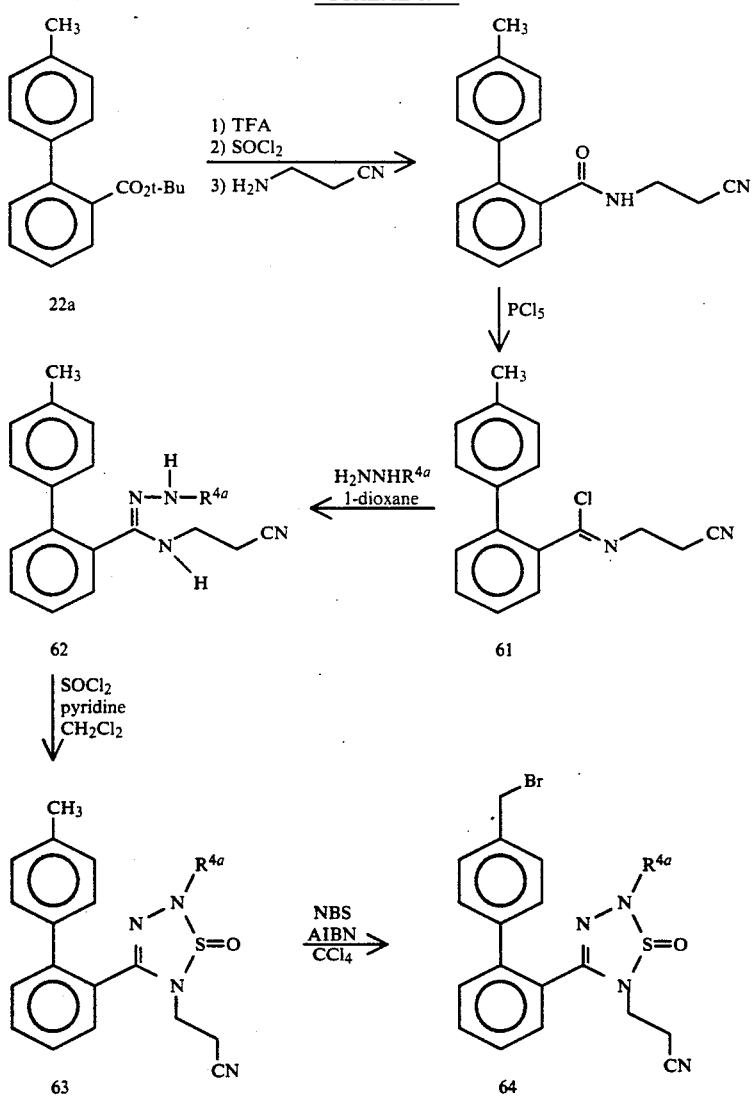

SCHEME 20 -continued

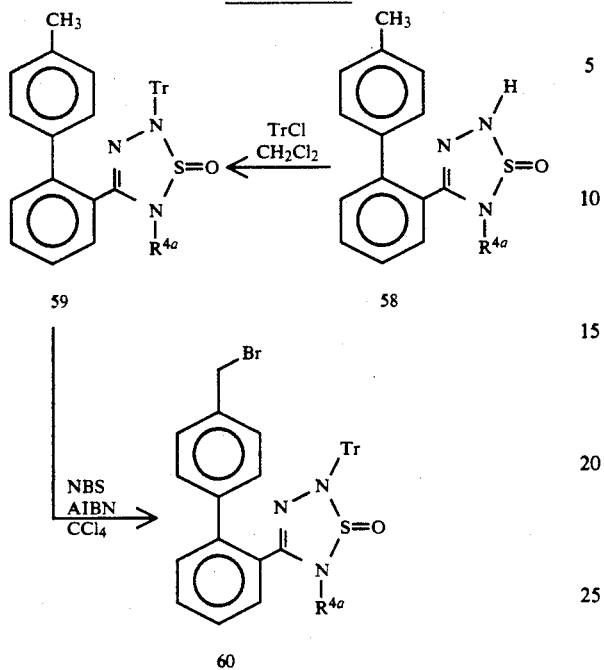

SCHEME 21

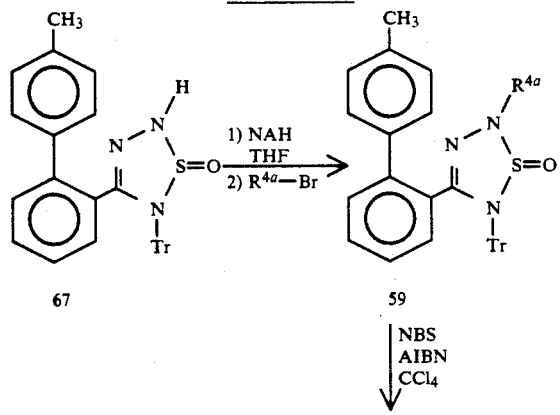

-continued SCHEME 21

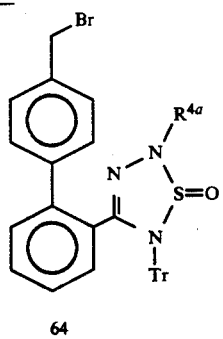

Compounds of Formula (I) and the benzyl halides of formula (3) wherein $R^1$ is 1,2,3,5-thiatriazole-1,1-dioxide-4-yl may be prepared using procedures described in *Monatsh. Chem.*, 1985, 116, pp 1321 and described herein. Sequential treatment of intermediates such as (61) or (57) with n-BuLi and $SO_2F_2$ will provide the 1,2,3,5-thiatriazol-1,1-dioxide analogs of (58) and (62). Further elaboration of the afore mentioned analogs by the methods described for the conversion of (58) to (60) in Scheme 18 and the methods described for the conversion of (62) to (64) in Scheme 19 would give the benzyl halides of formula (3) wherein $R^1$ is 2-triphenylmethyl-1,2,3,5-thiatriazole-1,1-dioxide-4-yl and 5-triphenylmethyl-1,2,3,5-thiatriazole-1,1-dioxide-4-yl, respectively.

Compound of Formula (I) wherein $R^1$ is 3-oxo-1,2,4-thiadiazolidine-1,1-dioxide may be prepared from the nitro derivative (22c) as outlined in Scheme 22. The amino compound 68 obtained from 7c may be reacted with t-butyl sulfamoylchloride to form the intermediate 69, which then can be alkylated with an appropriate bromoacetic acid derivative to give 70. Treatment of 70 with trifluoroacetic acid followed by the treatment with an appropriate base such as sodium or potassium alkoxide may produce the desired compound 71, which can be elaborated further to give the key alkylating agent 73 as outline in the scheme. Alkylation of an appropriate heterocyclic compound with 73 may then furnish the desired antagonist.

SCHEME 22

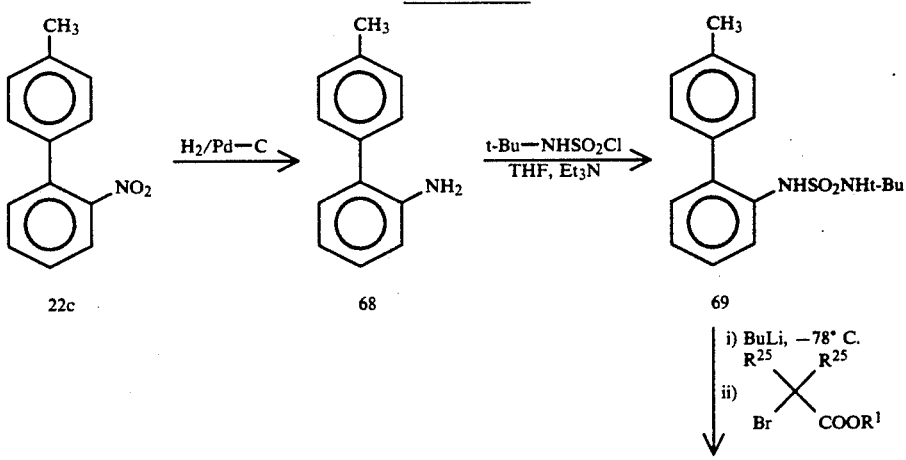

SCHEME 22 -continued

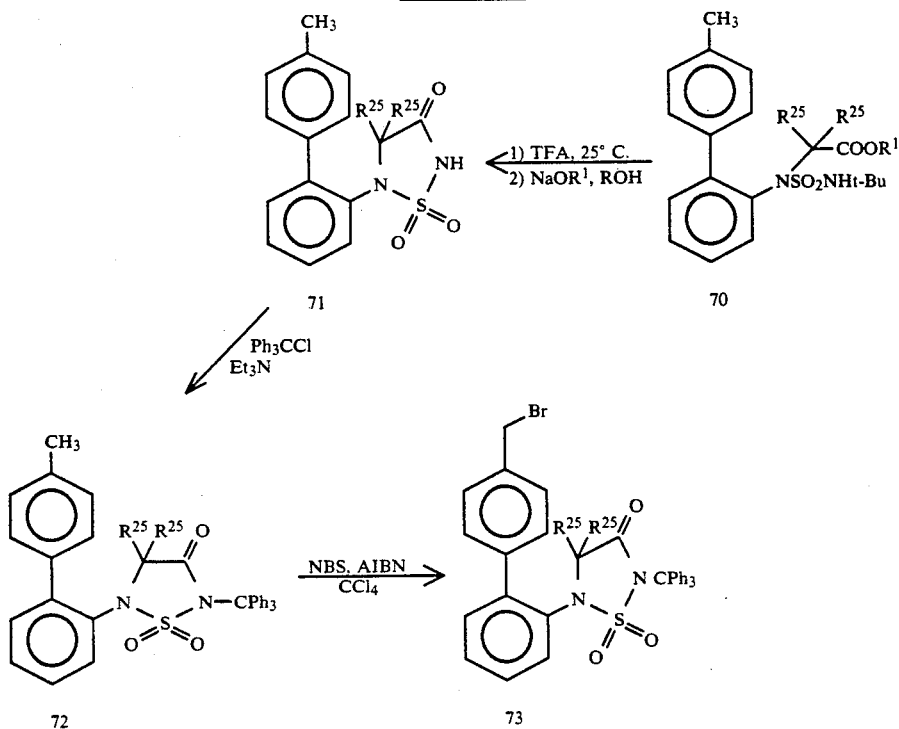

Compound of Formula (I) wherein $R^1$ is 5-aminosulfonyl-1,2,4-oxadiazole may be prepared using the bromomethyl biphenyl derivative 77 and an appropriate heterocyclic compound. The synthesis of 77 can be accomplished as outlined in Scheme 23. The amidoxime 53 may be reacted with S-methylisothiourea to form the 5-amino-1,2,4-oxadiazole 74, which can be then treated with an appropriate sulfonylchloride to give the corresponding 5-aminosulfonyl-1,2,4-oxadiazole 75. The appropriately protected derivative 76 then can be brominated to form the desired alkylating agent 77.

SCHEME 23

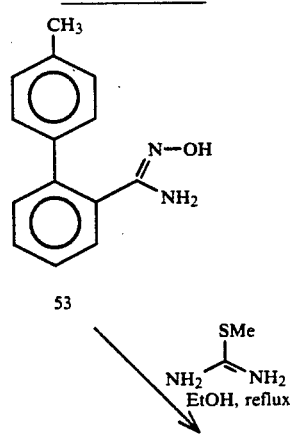

SCHEME 23

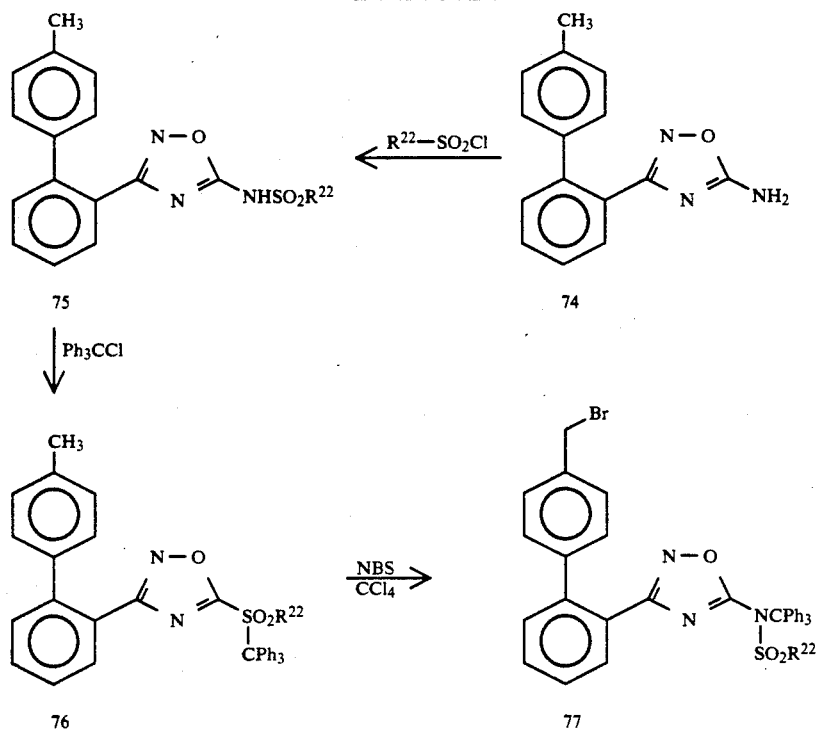

Compounds of Formula (I) wherein R¹ is 3-aminosulfonyl-1,2,4-oxadiazole can be prepared starting from the carboxylate derivative (22a) as outlined in Scheme 24. The ester derivative 78 obtained from 22a is treated with N-hydroxy guanidine sulfate in the presence of an alkoxide base to form the 3-amino-1,2,4-oxadiazole derivative 79, which may be reacted with an appropriate sulfonyl chloride to give the 3-aminosulfonyl-1,2,4-oxadiazole compound 80. The compound 81 can be prepared from 80 as outlined in Scheme 24.

SCHEME 24

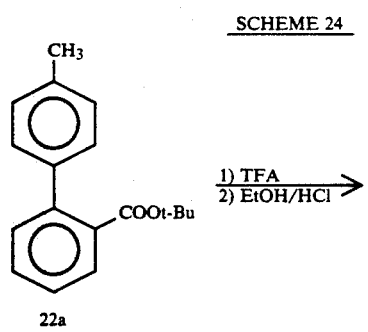

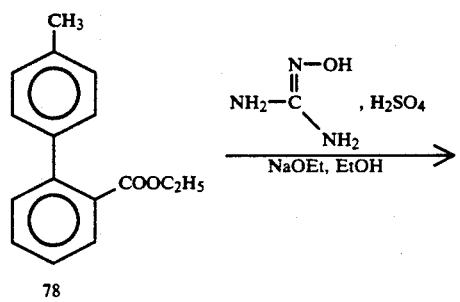

-continued
SCHEME 24

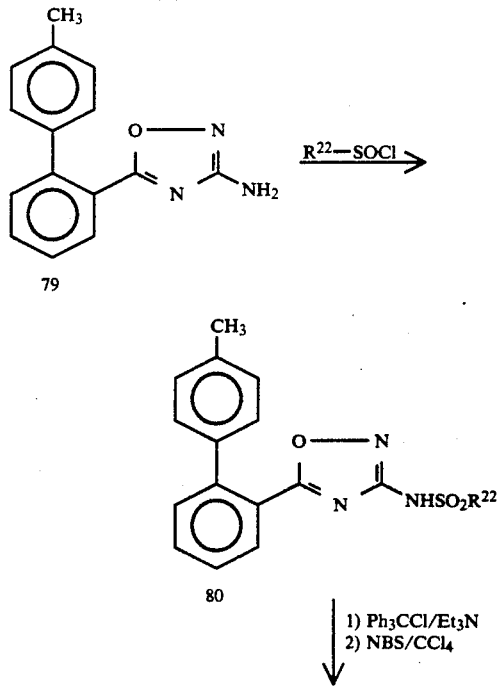

SCHEME 24 -continued

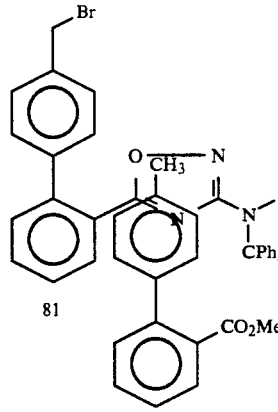

81

SCHEME 25

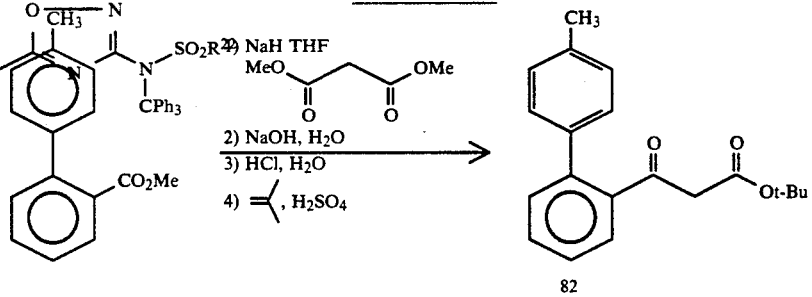

extrude $CO_2$ and iso-butene, then treated with base such as KOH to form the oxathiazolinone dioxide intermediate (83). Treatment of (83) with triphenylmethyl chloride and triethylamine in $CH_2Cl_2$ gives (84) which in turn is converted to benzyl halide (85) by treatment with N-bromosuccinimide, AIBN, in $CCl_4$ at reflux.

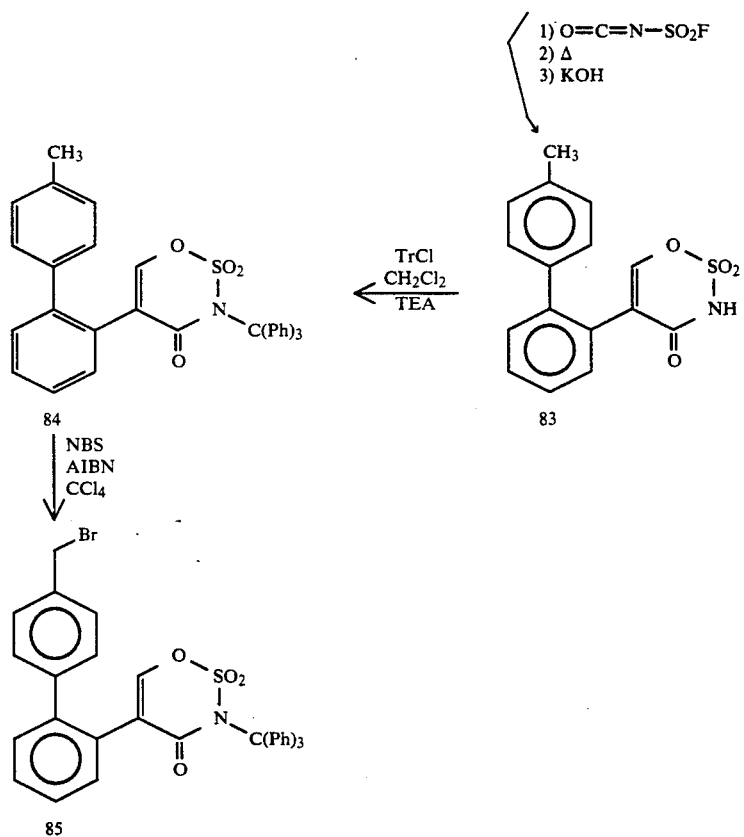

Compounds of Formula (I) and the benzyl halides of formula (3) wherein $R^1$ is 1,2,3-oxathiazin4(3H)-one-2,2-dioxide-6-yl may be prepared as outlined in Scheme 25. As shown and according to procedures in *Angew. Chem. Int. Edn.*, (1973), 12, pp 869, the betaketoester (82) is treated with fluorosulphonyl isocyante, heated to Compounds of Formula (I) wherein $R^1$ is oxamic acid may be prepared utilizing procedures described in J. Med. Chem., 1981, 24, pp 742-748 and as outlined in Scheme 26. The amine (46) is reacted with ethyl oxalyl chloride in the presence of a base such as pyridine or triethylamine and a solvent such as $CH_2Cl_2$ to form the intermediate oxalyl ester which is subsequently saponified with hydroxide to form oxamic acid (86).

SCHEME 26

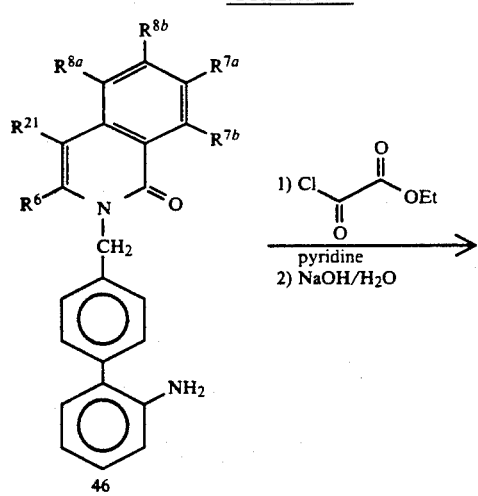

SCHEME 27

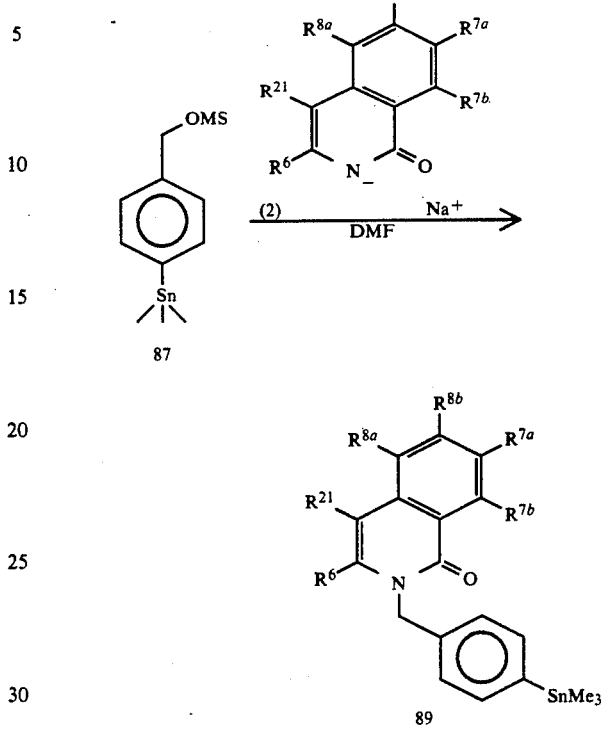

Compounds of Formula (I) wherein $R^1$ is -SO$_2$NR-$^{22a}$OR$^{22a}$ may be prepared as outlined in Scheme 27. The key intermediate 89 is prepared by the reaction of an appropriate heterocyclic compound (2), preferably as an alkali metal salt, with the alkylating agent 87 (prepared from 36). The compound 91, prepared from the sulfonyl chloride 90 and O-t-butylhydroxylamine, is then reacted with 89 in the presence of a Pd(0) catalyst to give 92. Removal of the t-butyl protecting group produces the desired N-hydroxy sulfonamide 93.

SCHEME 27

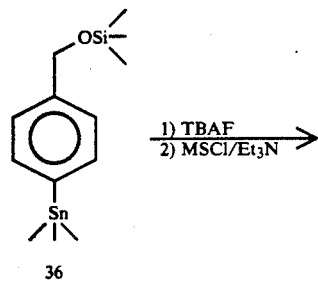

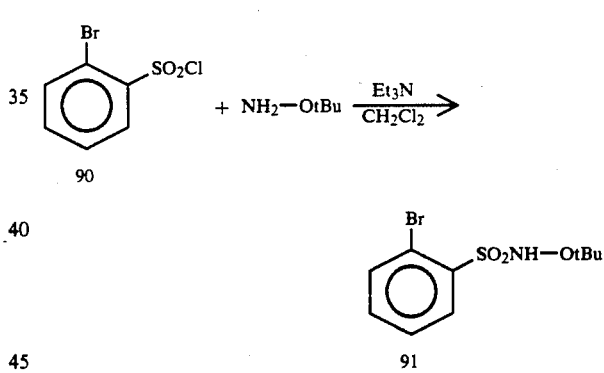

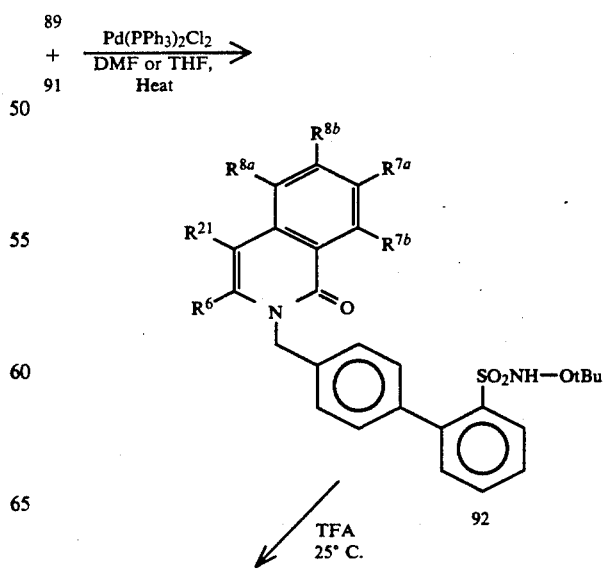

-continued
SCHEME 27

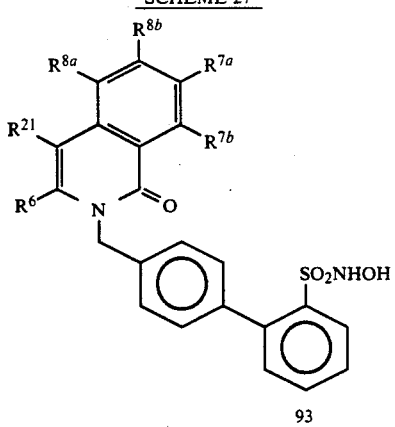

93

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I. For example, $R^1$ as carboxyl is often protected as its t-butyl ester which in the last step is removed by treatment with trifluoroacetic acid.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methane-sulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. In order to identify AII antagonists and determine their efficacy in vitro, the following two ligand-receptor binding assays were established.

Receptor Binding Assay Using Rabbit Aortae Membrane Preparation:

Three frozen rabbit aortae (obtained from Pel-Freeze Biologicals) are suspended in 5 mM Tris-0.25M Sucrose, pH 7.4 buffer (50 ml) homogenized, and then centrifuged. The mixture is filtered through a cheesecloth and the supernatant is centrifuged for 30 minutes at 20,000 rpm at 4° C. The pellet thus obtained is resuspended in 30 ml of 50 mM Tris-5 mM $MgCl_2$ buffer containing 0.2% Bovine Serum Albumin and 0.2 mg/ml Bacitration and the suspension is used for 100 assay tubes. Samples tested for screening are done in duplicate. To the membrane preparation (0.25 ml) there is added $^{125}$I-Sar$^1$Ile$^8$-angiotensin II [obtained from New England Nuclear] (10 ul; 20,000 cpm) with or without the test sample and the mixture is incubated at 37° C. for 90 minutes. The mixture is then diluted with ice-cold 50 mM Tris-0.9% NaCl, pH 7.4 (4 ml) and filtered through a glass fiber filter (GF/B Whatman 2.4" diameter). The filter is soaked in scintillation cocktail (10 ml) and counted for radioactivity using Packard 2660 Tricarb liquid scintillation counter. The inhibitory concentration ($IC_{50}$) of a potential AII antagonist which gives 50% displacement of the total specifically bound $^{125}$I-Sar$^1$Ile$^8$-angiotensin II is presented as a measure of the efficacy of such compounds as AII antagonists.

Receptor Assay Using Bovine Adrenal Cortex Preparation

Bovine adrenal cortex is selected as the source of AII receptor. Weighed tissue (0.1 g is needed for 100 assay tubes) is suspended in Tris.HCl (50 mM), pH 7.7 buffer and homogenized. The homogenate is centrifuged at 20,000 rpm for 15 minutes. Supernatant is discarded and pellets resuspended in buffer [$Na_2HPO_4$ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there is added 3H-angiotensin II (50 mM) (10 ul) with or without the test sample and the mixture is incubated at 37° C. for 1 hour. The mixture is then diluted with Tris buffer (4 ml) and filtered through a glass fiber filter (GF/B Whatman 2.4" diameter). The filter is soaked in scintillation cocktail (10 ml) and counted for radioactivity using Packard 2660 Tricarb liquid scintillation counter. The inhibitory concentration ($IC_{50}$) of a potential AII antagonist which gives 50% displacement of the total specifically bound $^3$H-angiotensin II is presented as a measure of the efficacy of such compounds as AII antagonists.

Receptor Assay Using Rat Brain Membrane Preparation

Membranes from rat brain (thalamus, hypothalamus and midbrain) are prepared by homogenization in 50 mM Tris HCl (pH 7.4), and centrifuged at 50,000×g. The resulting pellets are washed twice in 100 mM NaCl, 5 mM $Na_2$.EDTA, 10 mM $Na_2HPO_4$ (pH 7.4) and 0.1 mM PMSF by resuspension and centrifugation. For binding assays, the pellets are resuspended in 160 volumes of binding assay buffer (100 mM NaCl, 10 mM $Na_2HPO_4$, 5 mM $Na_2$.EDTA, pH 7.4, 0.1 mM PMSF, 0.2 mg/ml soybean trypsin inhibitor, 0.018 mg/ml o-phenanthroline, 77 mg/ml dithiothreitol and 0.14 mg/ml bacitracin. For $^{125}$I.Ile$^8$-angiotensin II binding assays, 10 μl of solvent (for total binding), Sar$^1$,Ile$^8$-angiotensin II (1 μM) (for nonspecific binding) or test compounds (for displacement) and 10 μl of [$^{125}$I]Sar$^1$-,Ile$^8$-angiotensin II (23-46 pM) are added to duplicate tubes. The receptor membrane preparation (500 μl) is added to each tube to initiate the binding reaction. The reaction mixtures are incubated at 37° C. for 90 minutes. The reaction is then terminated by filtration under reduced pressure through glass-fiber GF/B filters and washed immediately 4 times with 4 ml of 5 mM ice-cold Tris HCl (pH 7.6) containing 0.15M NaCl. The radioactivity trapped on the filters is counted using a gamma counter.

Using the methodology described above, representative compounds of this invention could be evaluated and an $IC_{50} < 50$ $\mu$M determined, thereby demonstrating and confirming the utility of the compounds of the invention as effective A II antagonists.

The antihypertensive effects of the compounds described in the present invention may be evaluated using the methodology described below: Male Charles River Sprague-Dawley rats (300-375 gm) are anesthetized with methohexital (Brevital; 50 mg/kg i.p.) and the trachea is cannulated with PE 205 tubing. A stainless steel pithing rod (1.5 mm thick, 150 mm long) is inserted into the orbit of the right eye and down th spinal column. The rats are immediately placed on a Harvard Rodent Ventilator (rate—60 strokes per minute, volumn—1.1 cc per 100 grams body weight). The right carotid artery is ligated, both left and right vagal nerves are cut, and the left carotid artery is cannulated with PE 50 tubing for drug administration, and body temperature is maintained at 37° C. by a thermostatically controlled heating pad which received input from a rectal temperature probe. Atropine (1 mg/kg i.v.) is then administered, and 15 minutes later propranolol (1 mg/kg i.v.). Thirty minutes later antagonists of formula I are administered intravenously or orally. Angiotensin II is then typically given at 5, 10, 15, 30, 45 and 60 minute intervals and every half-hour thereafter for as long as the test compound showed activity. The change in the mean arterial blood pressure is recorded for each angiotensin II challenge and the precent inhibition of the angiotensin II response is calculated.

The compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Perferably, the dosage range will be about 2.5 to 250 mg. per patient per day; more preferably about 5 to 150 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, rauwolfia serpentina, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250-350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Perferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptylphysostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15-200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the unit dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The following examples further illustrate the preparation of the compounds of Formula I and their incorporation into pharmaceutical compositions and, as such, are not to be considered or construed as limiting the invention recited in the appended claims.

EXAMPLE 1

Preparation of
4'-bromomethylbiphenyl-2-tert-butylsulfonamide

Step 1: Preparation of
2-bromobenzene(tert-butyl)-sulfonamide

To a stirred solution of 2-bromobenzenesulfonyl chloride (Lancaster Synthesis) (2.21 g, 8.65 mmol) in chloroform (40 ml) under nitrogen at room temperature was added tert-butylamine (Aldrich) (2.30 ml, 21.9 mmol). The orange solution was stirred at room temperature for 12 h, then the mixture evaporated to dryness. Flash chromatography (silica gel, 10,15% ethyl acetate-hexane) afforded 2-bromobenzene(tertbutyl)sulfonamide as a white solid; $^1$H NMR (300 MHz, CDCl$_3$) δ 8.18 (d, J=8.5 Hz, 1H), 7.73 (d, J=8.5 Hz, 1H), 7.50-7.35 (m, 2H), 5.11 (s, 1H), 1.20 (s, 9H).

Step 2: Preparation of p-tolyltrimethyltin p-Tolylmagnesium bromide solution (Aldrich) (1.0M solution in diethyl ether) (53 ml, 0.0530 mol) was added dropwise to trimethyltin chloride (6.92 g, 0.0347 mol) in tetrahydrofuran (50 ml) under nitrogen at −10° C. The suspension was allowed to warm slowly to room temperature over 3 h then saturated ammonium chloride solution (10 ml) was added followed by sufficient water to dissolve the precipitate. The solution was extracted three times with diethyl ether-hexane (1:1). The combined organic phase was washed with brine, dried (magnesium sulfate) and the solvents removed in vacuo. Vacuum distillation of the residue afforded a colorless liquid (39°-40° C., 0.1 mm Hg) which was further purified by flash chromatography (silica gel, hexane) to give p-tolyltrimethyltin as a colorless liquid; $^1$H NMR (300 MHz, CDCl$_3$) δ 7.40 (d, J=7.7 Hz, 2H), 7.19 (d, J=7.7 Hz, 2H), 2.34 (s, 3H), 0.30 (s, 9H).

Step 3: Preparation of
4'-methylbiphenyl-2-tertbutylsulfonamide

2-Bromobenzene(tert-butyl)sulfonamide (1.00 g, 3.92 mmol), p-tolyl-trimethyltin (1.95 g, 6.67 mmol), bis(triphenylphosphine)palladium(II) chloride (Aldrich) (165 mg, 0.235 mmol) and dimethylformamide (25 ml) were heated with stirring under nitrogen at 90° C. for 5 h. The black suspension was cooled to room temperature, then filtered through a pad of celite which was washed with tetrahydrofuran. The colorless filtrate was evaporated to dryness then chromatographed (silica gel, 8,10% ethyl acetate-hexane) to give 4'-methylbiphenyl-2-tert-butylsulfonamide as a white solid; $^1$H NMR (300 MHz, CDCl$_3$) δ 8.16 (d, J=7.9 Hz, 1H), 7.60-7.37 (m, 4H), 7.36-7.24 (m, 3H), 3.57 (s, 1H), 2.42 (s, 3H), 0.99 (s, 9H).

Step 4: Preparation of
4'-bromomethylbiphenyl-2-tertbutylsulfonamide

N-Bromosuccinimide (0.387 g, 2.17 mmol), a,a'-azoisobutyronitrile (catalytic), 4'-methylbiphenyl-2-tert-butylsulfonamide (0.55 g, 1.81 mmol) and carbon tetrachloride (50 ml) were heated with stirring at reflux for 3 h. After cooling to room temperature the mixture was filtered and the filtrate evaporated to dryness. Flash chromatography (silica gel, 10,20% ethyl acetate-hexane) afforded 4'-bromomethylbiphenyl-2-tert-butylsulfonamide (77% pure (the remainder of the material was 4'-dibromomethylbiphenyl-2-tert-butylsulfonamide)) as a white solid; $^1$H NMR (300 MHz, CDCl$_3$) δ 8.17 (dd, J=7.5, 1.6 Hz, 1H), 7.68-7.45 (m, 6H), 7.31 (dd, J=7.5, 1.6 Hz, 1H), 4.55 (s, 2H), 3.52 (s, 1H), 1.00 (s, 9H).

EXAMPLE 2

Preparation of
4'-bromomethylbiphenyl-2-(O-tertbutyl)-N-hydroxysulfonamide

Step 1: Preparation of
2-bromobenzene(O-tertbutyl)-N-hydroxysulfonamide

To a stirred solution of 2-bromobenzenesulfonyl chloride (Lancaster Synthesis) (1.0 g, 4.0 mmol) in chloroform (10 ml) under nitrogen at 0° C. was added O-tert-butylhydroxylamine hydrochloride (Fluka) (0.6 g, 4.77 mmol) in three portions. The solution was stirred at room temperature for 18 h and then diluted with methylene chloride (20 ml). The organic phase was washed successively with 5% citric acid, water and then dried over MgSO$_4$. Removal of the solvent in vacuo gave the crude product as white solid, which was then purified by flash chromatography (silica gel, 10% ethyl acetate-hexane) to afford 2-bromobenzene(O-tert-butyl)N-hydroxysulfonamide (1.12 g, 89%) as a white solid;

$^1$H NMR (300 MHz, CDCl$_3$) δ 8.15 (dd, J=7.5, 2.1 Hz, 1H), 7.75 (d, J=7.6, 1.8 Hz, 1H), 7.55–7.35 (m, 3H), 5.11 (s, 1H), 1.21 (s, 9H). FAB-MS: 309 (M+H).

Step 2: Preparation of
4′-methylbiphenyl-2-(O-tert-butyl)-N-hydroxy sulfonamide

A solution of 2-bromobenzene(O-tert-butyl)-N-hydroxysulfonamide (0.31 g, 1.0 mmol), p-tolyltrimethyltin (0.3 g, 1.18 mmol) and bis(triphenylphosphine)palladium(II) chloride (Aldrich) (0.036 g) in dry dimethylformamide (6 ml) was stirred under nitrogen at 90° C. for 6 h. The black suspension was cooled to room temperature, then filtered through a pad of celite which was washed with tetrahydrofuran. The colorless filtrate was evaporated to dryness then purified by flash chromatography (silica gel, 8% ethyl acetate-hexane) to give the titled compound as a semi-solid mass. $^1$H NMR (300 MHz, CDCl$_3$) δ 8.15 (d, J=7.8, 1.6 Hz, 1H), 7.67–7.50 (m, 2H), 7.36–7.24 (m, 5H), 5.78 (s, 1H), 2.42 (s, 3H), 1.08 (s, 9H). FAB-MS: 320 (M+H).

Step 3: Preparation of
4′-bromomethylbiphenyl-2-(O-tert-butyl)-N-hydroxysulfonamide A mixture of N-Bromosuccinimide (0.14 g, 0.78 mmol), a,a′-azoisobutyronitrile (10 mg) and 4′-methylbiphenyl-2-(O-tert-butyl)-N-hydroxy sulfonamide (0.25 g, 0.78 mmol) in carbon tetrachloride (10 ml) was refluxed for 7 h. After cooling to room temperature the mixture was filtered and the filtrate evaporated to dryness. Flash chromatography (silica gel, 10% ethyl acetate-hexane) afforded 4′-methylbiphenyl-2-(O-tert-butyl)-N-hydroxy sulfonamide as a white solid. $^1$H NMR (300 MHz, CDCl$_3$) δ 8.15 (d, J=7.8 Hz, 1H), 7.70–7.30 (m, 7H), 5.72 (s,1H), 4.55 (s, 2H), 1.08 (s, 9H). FAB-MS: 398, 400 (M+H).

EXAMPLE 3

3-Butyl-1(2H)-isoquinolinone

To a solution of 4 g (24 mmol) of homophthalic anhydride in 12 ml of dry pyridine in a 250 L 3 neck flask fitted with a reflux condenser and addition funnel at 0° C. was added 5.4 g (45 mmol) of valeryl chloride in 16 ml of dry chloroform over 45 minutes. The reaction mixture was stirred for a further 1 hour and then was treated with 100 ml of conc. ammonium hydroxide dropwise. The mixture was refluxed for 2 hours and then allowed to stand overnight at room temperature. The two phases were separated and the organic phase was washed with water (1×20 ml). The organic phase was dried over MgSO$_4$, filtered and concentrated in vacuo. The residue was recrystallized from hot MeOH/water to give a pale purple solid.

$^1$H-NMR (CDCl$_3$): 0.96 (t, 3H, J=7.2 Hz), 1.45 (m, 2H), 1.73 (m, 2H), 2.64 (3 line m, 2H, J=7.8 Hz), 6.32 (s, 1H), 7.37–7.67 (m, 3H), 8.37 (d, 1H, J=7.8 Hz). FABMS: 202 (M$^+$+1).

EXAMPLE 4

7-Nitro-3-propyl-1(2H)-isoquinolinone

To a mixture of 50 ml of butyric anhydride and 10 ml of pyridine in a dry flask was added 10 g (0.45 mol) of 4-nitrohomophthalic anhydride (prepared as in *J. Org. Chem.*, 533, 1945). A thick red suspension formed which prevented efficient stirring. 50 ml of ether was added to facilitate stirring. After 3 hours the reaction mixture was filtered and the precipitate was washed with ether. The residue was dried under vacuum to give 15.3 g of a red solid. The solid was suspended in 250 ml of ammonium hydroxide and heated to 80° C. for 3 hours. Further 20 ml portions of ammonium hydroxide were added at 45 minute intervals. The mixture was cooled to room temperature and filtered. The residue was recrystallized from hot ethanol to give yellow crystals.

$^1$H-NMR (CDCl$_3$): 1.04 (t, 3H, J=7.4 Hz), 1.79 (m, 2H), 2.62 (3 line m, 2H, J=7.6 Hz), 6.37 (s, 1H), 7.57 (d, 1H, J=8.8 Hz), 8.39 (dd, 1H, J=2.4, 8.8 Hz), 9.20 (d, 1H, J=2.1 Hz).

EXAMPLE 5

3-Butyl-2-[(2′-(t-butoxycarbonyl)biphen-4-yl)methyl]-1-isoquinolinone

To a suspension of sodium hydride in dry DMF at 0° C. is added 3-n-butyl-1(2H)-isoquinolinone as a solid. The solid dissolves with evolution of H$_2$ gas. 4′-Bromomethyl-2′-t-butoxycarbonylbinylbiphenyl is added dissolved in DMF to the above the reaction mixture which is stirred overnight. The solution after dilution with EtOAc, is washed with water and brine, dried over MgSO$_4$ and concentrated in vacuo. The product is purified by flash chromatography over silica.

EXAMPLE 6

3-Butyl-2-(2′-(amino-sulfonylbiphen-4-yl)methyl)-1-isoquinolinone

Step 1:
3-Butyl-2-(2′-((tert-butylamino)sulfonyl-biphen-4-yl)methyl)-1-isoquinolinone 3-Butyl-1(2)-isoquinolinone from Example 3 is added to a stirred suspension of sodium hydride in dimethylformamide at room temperature under nitrogen. The mixture is heated at 50° C. then cooled to room temperature. A solution of 4′-(bromomethyl)-biphenyl-2-tert-butylsulfonamide in dimethylformamide is then added dropwise to the reaction mixture and the mixture is stirred at room temperature overnight. After removal of the solvent in vacuo, the residue obtained is purified by flash chromatography (silica gel) to give the titled compound.

Step 2:
3-Butyl-2-(2′-(aminosulfonyl-biphen-4-yl)-methyl)-1-isoquinolinone

The compound from Step 1 is dissolved in trifluoroacetic acid and anisole is added at room temperature. The solution is stirred under nitrogen at room temperature. After removal of the solvent in vacuo, the crude product obtained is purified by flash chromatography to provide the desired product.

EXAMPLE 7

3-Butyl-2-(2'-((isopropylsulfonylamino)sulfonylbiphen-4-yl)methyl)-1-isoquinolinone To a stirred suspension of NaH in dry DMF under nitrogen at room temperature is added the compound from Example 6. After stirring for 30 minutes at room temperature, isopropylsulfonylchloride is added, and the resulting mixture is stirred at room temperature overnight. The reaction mixture is poured into ice water, acidified with 5% citric acid solution and extracted with chloroform. The organic phase is washed with water and brine, and then dried over MgSO₄. The crude product obtained after removal of the solvent is purified by flash-chromatography to give the desired product.

EXAMPLE 8

3-Butyl-2-(2'-((dibenzylphosphonylamino)sulfonylbiphen-4-yl)methyl)-1-isoquinolinone To a stirred solution of the compound from Example 6 in dry THF is added n-BuLi at 0° C. After stirring fo 15 minutes at that temperature, a solution of dibenzylphosphorylchloride in THF is added. The resulting mixture is then stirred at room temperature overnight. The reaction mixture is concentrated under reduced pressure, and the residue obtained is treated with 5% citric acid solution and extracted with methylene chloride. The organic phase is washed with water and brine, and then dried over MgSO₄. The crude product obtained after removal of the solvent is purified on silica-gel by flash-chromatography to give the titled product.

EXAMPLE 9

3-Butyl-2-((N-hydroxyamino)sulfonylbiphen-4-yl)-methyl)-1-isoquinolinone

Step 1:
3-Butyl-2-(2'-((O-tert-butyl-N-hydroxyamino)sulfonyl-biphen-4-yl)methyl)-1-isoquinolinone 3-Butyl-1(2H)-isoquinolinone is added at room temperature to a stirred suspension of sodium hydride (60% dispersion) in dimethylformamide under nitrogen. The mixture is stirred at room temperature and then a solution of 4'-bromomethylbiphenyl-2-(O-tert-butyl)-N-hydroxysulfonamide in dimethylformamide is added. The reaction is stirred at room temperature overnight. The solvent is removed in vacuo and the crude product obtained is purified by flash chromatography (silica gel) to give the titled compound.

Step 2:
3-Butyl-2-(2'-((N-hydroxyamino)sulfonylbiphen-4-yl)methyl)-1-isoquinolinone Anisole is added to a stirred solution of the compound from Step 1 in trifluoroacetic acid and the solution was stirred at room temperature. The solvent is removed in vacuo and the residue is triturated with dry ether and filtered to give the desired product.

EXAMPLES 10 TO 19

The compounds of the Formula (II) exemplified in Table B are prepared from the appropriate substituted starting materials utilizing the general procedures outlined in the above examples and the noted schemes.

TABLE B

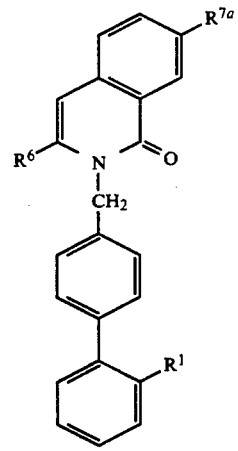

(II)

| Example # | R¹ | R⁶ | R⁷ᵃ | Scheme |
|---|---|---|---|---|
| 10 | —SO₂NHSO₂Me | Bu | Me | 9 |
| 11 | —SO₂NHSO₂iPr | Pr | Me | 9 |
| 12 | (structure) | Bu | Me | 18, 19 |
| 13 | (structure) | Pr | Me | 18–21 |
| 14 | —NH—C(=O)—COH(=O) | Bu | Me | 26 |
| 15 | —SO₂NHSO₂iPr | Bu | iPr | 9 |
| 16 | —SO₂NHPOCH₂Ph (OCH₂Ph) | Pr | Me | 14 |
| 17 | (structure) | Bu | Me | 22 |
| 18 | (structure, NHSO₂Ph) | Pr | Me | 12 |
| 19 | (structure) | Bu | Me | 16 |

FORMULATION EXAMPLES

Typical Pharmaceutical Compositions Containing a Compound of the Invention

A: Dry Filled Capsules Containing 50 mg of Active Ingredient Per Capsule

| Ingredient | Amount per capsule (mg) |
| --- | --- |
| 3-Butyl-2-(2'-(isopropyl-sulfonylamino)sulfonyl-biphenyl-4-yl)methyl-7-methyl-1-isoquinolinone | 50 |
| Lactose | 149 |
| Magnesium stearate | 1 |
| Capsule (size No. 1) | 200 |

3-Butyl-2-(2'-(isopropylsulfonylamino)-sulfonyl-biphenyl-4-yl)methyl-7-methyl-1-isoquinolinone (title compound of Example 11) can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 3-butyl-2-(2'-(isopropylsulfonylamino)-sulfonybiphenyl-4-yl)methyl-7-methyl-1-isoquinolinone (25 mg), pregelatinized starch USP (82 mg), microcrystaline cellulose (82 mg) and magnesium stearate (1 mg).

C: Combination Tablet

A typical combination tablet would contain, for example, a diuretic such as hydrochlorothiazide and consist of 3-butyl-2-(2'-(isopropylsulfonylamino)-sulfonyl-biphenyl-4-yl)methyl-7-methyl-1-isoquinolinone (7.5 mg), hydrochlorothiazide (50 mg) pregelatinized starch USP (82 mg), microcrystalline cellulose (82 mg) and magnesium stearate (1 mg).

D: Suppository

Typical suppository formulations for rectal administration can contain 3-butyl-2-(2'-(isopropylsulfonylamino)-sulfonylbiphenyl-4-yl)methyl-7-methyl-1-isoquinolinone (1–25 mg), butylated hydroxyanisole (0.08–1.0 mg), disodium calcium edetate (0.25–0.5 mg), and polyethylene glycol (775–1600 mg). Other suppository formulations can be made by substituting, for example, butylated hydroxytoluene (0.04–0.08 mg) for the disodium calcium edetate and a hydrogenated vegetable oil (675–1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectable formulation would contain 3-butyl-2-(2'-(isopropylsulfonylamino)-sulfonylbiphenyl-4-yl)methyl-7-methyl-1-isoquinolinone (5.42 mg), sodium phosphate dibasic anhydrous (11.4 mg) benzyl alcohol (0.01 ml) and water for injection (1.0 ml). Such an injectable formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of the Formula (I)

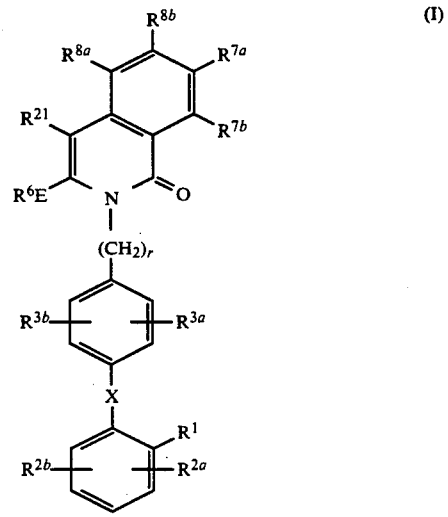

or a pharmaceutically acceptable salt thereof, wherein:

$R^1$ is (a) $-SO_2N(R^{22a})-OR^{22a}$, (b) $-SO_2NHSO_2R^{22}$, (c)

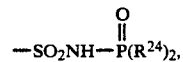

(d)

(e) $-SO_2NHCN$, (f) $-SO_2NHCO_2R^{22}$, (g) $-NHSO_2NHSO_2R^{22}$, (h) 

(i) 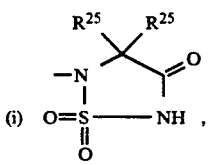

(j) 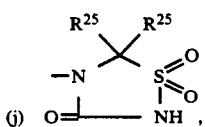

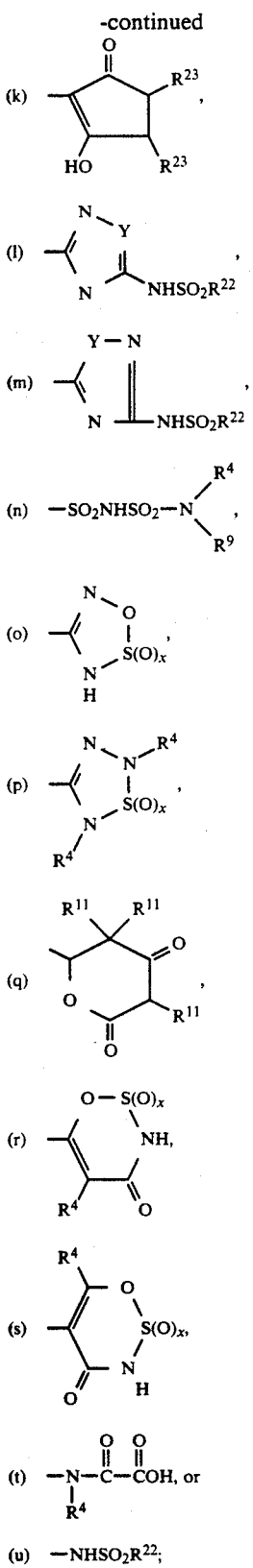

wherein
Y is O or S;
$R^{2a}$ and $R^{2b}$ are each independently
(a) H,
(b) Cl, Br, I, or F,
(c) $NO_2$,
(d) $NH_2$,
(e) $C_1$–$C_4$-alkylamino,
(f) di($C_1$–$C_4$-alkyl)amino,
(g) $SO_2NHR^9$,
(h) $CF_3$,
(i) $C_1$–$C_6$-alkyl,
(j) $C_1$–$C_6$-alkoxy,
(k) $C_1$–$C_6$-alkyl-S-,
(l) $C_2$–$C_6$-alkenyl,
(m) $C_2$–$C_6$-alkynyl;
(n) aryl,
(o) aryl($C_1$–$C_4$-alkyl), or
(p) $C_3$–$C_7$-cycloalkyl;

$R^{3a}$ is
(a) H,
(b) Cl, Br, I, or F,
(c) $C_1$–$C_6$-alkyl,
(d) $C_1$–$C_6$-alkoxy, or
(e) $C_1$–$C_6$-alkoxyalkyl;

$R^{3b}$ is
(a) H,
(b) Cl, Br, I, or F,
(c) $NO_2$,
(d) $C_1$–$C_6$-alkyl,
(e) $C_1$–$C_6$-acyloxy,
(f) $C_3$–$C_7$-cycloalkyl,
(g) $C_1$–$C_6$-alkoxy,
(h) -$NHSO_2R^4$,
(i) hydroxy($C_1$–$C_4$-alkyl),
(j) aryl($C_1$–$C_4$-alkyl),
(k) $C_1$–$C_4$-alkylthio,
(l) $C_1$–$C_4$-alkyl sulfinyl,
(m) $C_1$–$C_4$-alkyl sulfonyl,
(n) $NH_2$,
(o) $C_1$–$C_4$-alkylamino,
(p) di($C_1$–$C_4$-alkyl)amino,
(q) fluoro-$C_1$–$C_4$-alkyl-,
(r) -$SO_2$-$NHR^9$,
(s) aryl,
(t) furyl,
(u) $CF_3$,
(v) $C_2$–$C_6$-alkenyl, or
(w) $C_2$–$C_6$-alkynyl;

wherein aryl is phenyl or naphthyl, or a substituted phenyl or naphthyl with one or two substituents selected from the group consisting of Cl, Br, I, F, $N(R^4)_2$, $CO_2R^4$, $C_1$–$C_4$-alkyl, $C_1$–$C_4$-alkoxy, $NO_2$, $CF_3$, $C_1$–$C_4$-alkylthio, OH, -$SO_2NR^9R^{10}$, $C_3$–$C_7$-cycloalkyl, $C_3$–$C_{10}$-alkenyl, or -SO($C_1$–$C_4$-alkyl);

$R^4$ is H, aryl, $C_1$–$C_6$ alkyl, or substituted $C_1$–$C_6$ alkyl in which substituent is aryl or heteroaryl, wherein heteroaryl is an unsubstituted, monosubstituted or disubstituted heteroaromatic 5 or 6 membered cyclic ring having one to three members selected from the group consisting of N, O, S, and wherein the substituents are members selected from the group consisting of -OH, -SH, $C_1$–$C_4$-alkyl, $C_1$–$C_4$-alkoxy, -$CF_3$, Cl, Br, I, F, or $NO_2$;

$R^{4a}$ is aryl, $C_1$–$C_6$-alkyl or a aryl-$C_1$–$C_6$-alkyl;

E is a single bond, -$NR^{13}(CH_2)_s$-, -$S(O)_x(CH_2)_s$- where x is 0 to 2 and s is 0 to 5, -CH(OH)-, —O—, or CO—;

$R^6$ is
(a) aryl,
(b) $C_1$–$C_6$-alkyl, $C_2$–$C_5$-alkenyl or $C_2$–$C_5$-alkynyl, or a substituted $C_1$–$C_6$-alkyl, a substituted $C_2$–$C_5$-alkenyl or a substituted $C_2$–$C_5$-alkynyl, in which the substituent is selected from the group consisting of aryl, $C_3$–$C_7$-cycloalkyl, Cl, Br, I, F, $CF_3$, $CF_2CF_3$, $-NH_2$, $-NH(C_1-C_4$-alkyl), $-OR^4$ $-N(C_1-C_4$-alkyl)$_2$, $-NH-SO_2R^4$, $-COOR^4$, or $-SO_2NHR^9$, (c) heteroaryl as defined hereinabove,
(d) $C_3$–$C_7$-cycloalkyl,
(e) perfluoro-$C_1$–$C_4$-alkyl, or
(f) H;

$R^{7a}$, $R^{7b}$, $R^{8a}$ and $R^{8b}$ are independently
(a) H,
(b) $C_1$–$C_8$-alkyl or a substituted $C_1$–$C_8$-alkyl with a substituent selected from the group consisting of -OH, -guanidino, $C_1$–$C_4$-alkoxy, $-N(R^4)_2$, $COOR^4$, $-CON(R^4)_2$, $-O-COR^4$, -aryl, -heteroaryl, $-S(O)_x-R^{22}$, -tetrazol-5-yl, $-CONHSO_2R^{22}$, $-SO_2NH$-heteroaryl, $-SO_2NHCOR^{22}$, $-PO(OR^4)_2$, $-PO(OR^4)R^9$, $-SO_2NH-CN$, $-NR^{10}COOR^{22}$, $-(CH_2)_{1-4}R^4$, $-COR^4$, $-CO$-heteroaryl, $-NR^4CONR^4R^{22}$ or $-NR^4COR^{22}$,
(c) -$C_3$–$C_7$-cycloalkyl,
(d) phenyl-$C_1$–$C_6$-alkyl or naphthyl-$C_1$–$C_6$-alkyl in which the phenyl or naphthyl group is unsubstituted or mono- or disubstituted with V or W,
(e) phenyl or naphthyl, or substituted phenyl or naphthyl in which the substituents are V or W,
(f) Cl, Br, I, F,
(g) $-OR^{22a}$,
(h) $-C_1$–$C_4$-perfluoroalkyl,
(i) $-S(O)_x-R^{22}$,
(j) $-COOR^4$,
(k) $-SO_3H$,
(l) $-NR^4R^{22}$,
(m) $-NR^{22a}COR^{22}$,
(n) $-NR^{22a}COOR^{22}$,
(o) $-SO_2NR^4R^9$,
(p) $-NO_2$,
(q) $-N(R^{22a})SO_2R^{22}$,
(r) $-NR^{22a}CONR^4R^{22}$,
(s)

(t) $-NHSO_2CF_3$,
(u) $-SO_2NH$-heteroaryl,
(v) $-SO_2NHCOR^{22}$,
(w) $-CONHSO_2R^{22}$,
(x) $-PO(OR^4)_2$,
(y) $-PO(OR^4)R^4$,
(z) -tetrazol-5-yl,
(aa) -CONH(tetrazol-5-yl),
(bb) $-COR^4$,
(cc) $-SO_2NHCN$
(dd) $-NR^4SO_2NR^4R^{22}$,
(ee) $-NR^4SO_2OR^{22}$
(ff) $-CONR^4R^{22}$,
(gg)

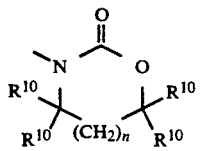

where n=0 or 1, or (hh)

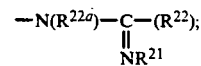

V and W are independently:
(a) hydrogen,
(b) $C_1$–$C_5$-alkoxy,
(c) $C_1$–$C_5$-alkyl,
(d) hydroxy,
(e) $C_1$–$C_5$-alkyl-$S(O)_x$-,
(f) CN,
(g) $NO_2$,
(h) $N(R^4)_2$,
(i) $CON(R^4)_2$,
(j) $CO_2R^4$,
(k) $COR^4$,
(l) $CF_3$,
(m) Cl, Br, I, or F,
(n) hydroxy-$C_1$–$C_5$-alkyl,
(o) $C_1$–$C_5$-alkylthio,
(p) $-SO_2NR^9R^{10}$,
(q) $C_3$–$C_7$-cycloalkyl, or
(r) $C_2$–$C_{10}$-alkenyl;

$R^9$ is H, $C_1$–$C_5$alkyl, aryl or arylmethyl;
$R^{10}$ is H, $C_1$–$C_4$-alkyl;
$R^{11}$ is H, $C_1$–$C_6$-alkyl, $C_1$–$C_4$-alkenyl, $C_1$–$C_4$-alkoxy alkyl, or

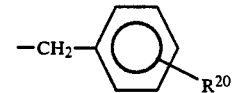

$R^{13}$ is H, ($C_1$–$C_4$-alkyl)CO-, $C_1$–$C_6$-alkyl, allyl, $C_3$–$C_6$-cycloalkyl, aryl or arylmethyl;
$R^{14}$ is H, $C_1$–$C_8$-alkyl, $C_1$–$C_8$-perfluoroalkyl, $C_3$–$C_6$-cycloalkyl, aryl or arylmethyl;
$R^{15}$ is H, $C_1$–$C_6$-alkyl;
$R^{16}$ is H, $C_1$–$C_6$-alkyl, $C_3$–$C_6$-cycloalkyl, aryl or arylmethyl;
$R^{17}$ is $-NR^9R^{10}$, $-OR^{10}$, $-NHCONH_2$, $-NHCSNH_2$,

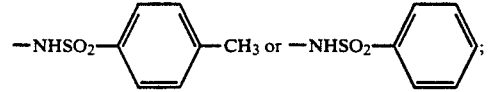

$R^{18}$ and $R^{19}$ are independently $C_1$–$C_4$-alkyl or taken together are $-(CH_2)_q$- where q is 2 or 3;
$R^{20}$ is H, $-NO_2$, $-NH_2$, $-OH$ or $-OCH_3$;
$R^{21}$ is
(a) H,
(b) Cl, F, Br or I,
(c) aryl,
(d) heteroaryl, or
(e) $C_1$–$C_4$-alkyl or a substituted $C_1$–$C_4$-alkyl with a substituent selected from the group consisting of aryl, heteroaryl, -OH, $-NH_2$, $-NH(C_1-C_4$-alkyl), $-N(C_1-C_4$-alkyl)$_2$, $-CO_2R^{4a}$, Cl, Br, F, I, or $-CF_3$;
$R^{22}$ is
(a) aryl,
(b) heteroaryl,
(c) $C_3$–$C_7$-cycloalkyl,
(d) $C_1$–$C_6$-alkyl or a substituted $C_1$–$C_6$-alkyl with one or two substituents selected from the group consisting of aryl, heteroaryl, -OH, -SH, $C_1$-$C_4$-alkyl, $C_3$-$C_7$-cycloalkyl, -O($C_1$-$C_4$-alkyl), -S($C_1$-$C_4$-alkyl), -$CF_3$, Cl, Br, F, I, -$NO_2$, -$CO_2H$, $CO_2$-($C_1$-$C_4$-alkyl), -$NH_2$, -NH($C_1$-$C_4$-alkyl), -N($C_1$-$C_4$-alkyl)$_2$, -$PO_3H_2$, -PO(OH)(O-$C_1$-$C_4$-alkyl), -PO($OR^4$)$R^9$, morpholinyl or $C_1$-$C_4$-alkylpiperazinyl, or (e) perfluoro-$C_1$-$C_4$-alkyl;

$R^{22a}$ is (a) hydrogen,
(b) aryl,
(c) heteroaryl,
(d) $C_3$-$C_7$-cycloalkyl,
(e) $C_1$-$C_6$-alkyl or a substituted $C_1$-$C_6$-alkyl with a substituent selected from the group consisting of aryl, heteroaryl, -OH, -SH, $C_1$-$C_4$-alkyl, -O($C_1$-$C_4$-alkyl), -S($C_1$-$C_4$-alkyl), -$CF_3$, Cl, Br, F, I, -$NO_2$, -$CO_2H$, $CO_2$-($C_1$-$C_4$-alkyl), -$NH_2$, -NH($C_1$-$C_4$-alkyl), -N($C_1$-$C_4$-alkyl)$_2$, -$PO_3H_2$, -PO(OH)(O-$C_1$-$C_4$-alkyl), -PO($OR^4$)$R^9$, morpholinyl or $C_1$-$C_4$alkylpiperazinyl, or
(f) perfluoro-$C_1$-$C_4$-alkyl;

$R^{23}$ is (a) H,
(b) aryl as defined above, or
(c) $C_1$-$C_6$-alkyl optionally substituted with aryl, F, Cl, Br, -OH, -$NH_2$, -NH($C_1$-$C_4$-alkyl), -N($C_1$-$C_4$-alkyl)$_2$, or $CF_3$;

$R^{24}$ is (a) aryl as defined above,
(b) $C_1$-$C_6$-alkyl optionally substituted with aryl, F, Cl, Br, -OH, -$NH_2$, -NH($C_1$-$C_4$-alkyl), -N($C_1$-$C_4$-alkyl)$_2$, $CF_3$, -$COOR^4$, or CN,
(c) -OCH($R^4$)-O-CO-$R^{4a}$, or
(d) -OH, -O-$C_1$-$C_6$-alkyl wherein alkyl is as defined in (b);

$R^{25}$ is (a) H,
(b) $C_1$-$C_6$-alkyl optionally substituted with aryl, F, Cl, Br, -OH, -$NH_2$, -NH($C_1$-$C_4$-alkyl), -N($C_1$-$C_4$-alkyl)$_2$, $CF_3$, -$COOR^4$, or CN, or
(c) F, Cl, Br;

X is (a) a carbon-carbon single bond,
(b) -CO-,
(c) -O-,
(d) -S-,
(e)

(f)

(g)

(h) -$OCH_2$-,
(i) -$CH_2O$-
(j) -$SCH_2$-, (k) -$CH_2S$-,
(l) -NHC($R^9$)($R^{10}$),
(m) -$NR^9SO_2$-,
(n) -$SO_2NR^9$-,
(o) -C($R^9$)($R^{10}$)NH-,
(p) -CH=CH-,
(q) -CF=CF-,
(r) -CH=CF-,
(s) -CF=CH-,
(t) -$CH_2CH_2$-,
(u) -$CF_2CF_2$-, (v) 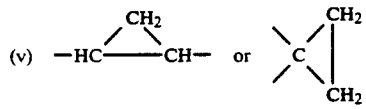

(w) 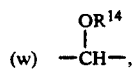

(x) 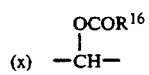

(y) 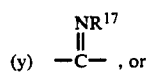 , or (z) 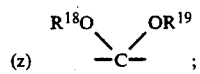 ;

and r is 1 or 2.

2. The compound of claim 1, wherein:

$R^1$ is:

(a) -$SO_2N(R^{22a})$-$OR^{22a}$,
(b) -$SO_2NHSO_2R^{22}$,
(c)

(d) -$SO_2NHCH$,
(e) -$SO_2NHCO_2R^{22}$,
(f)

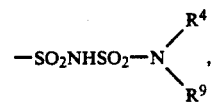

(g) -$NHSO_2NHSO_2R^{22}$,
(h)

(i) 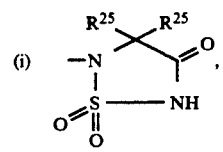

-continued (j) 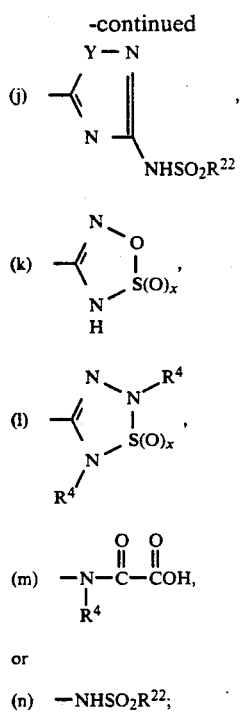

(k)

(l)

(m) 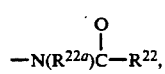

or (n) —NHSO$_2$R$^{22}$;

R$^{2a}$ is H;
R$^{2b}$ is H, F, Cl, CF$_3$, NO$_2$, C$_1$–C$_6$-alkyl, C$_2$–C$_6$-alkenyl, C$_2$–C$_6$-alkynyl, or aryl;
R$^{3a}$ is H;
R$^{3b}$ is H, F, Cl, CF$_3$, NO$_2$, C$_1$–C$_4$-alkyl, C$_2$–C$_4$-alkenyl, C$_2$–C$_4$-alkynyl, C$_5$–C$_6$-cycloalkyl, -COOCH$_3$, -COOC$_2$H$_5$, -SO$_2$-CH$_3$, NH$_2$, -N(C$_1$–C$_4$-alkyl)$_2$ or -NH-SO$_2$CH$_3$;
E is a single bond, —O— or —S—;
R$^6$ is
 (a) C$_1$–C$_5$ alkyl or a substituted C$_1$–C$_5$ alkyl with a substituent selected from the group consisting of C$_3$–C$_5$-cycloalkyl, Cl, CF$_3$, CCl$_3$, -O-CH$_3$, -OC$_2$H$_5$, -S-CH$_3$, -S-C$_2$H$_5$, phenyl, or F;
 (b) C$_2$–C$_5$-alkenyl or C$_2$–C$_5$-alkynyl; or,
 (c) C$_3$–C$_5$-cycloalkyl;
R$^{7a}$, R$^{7b}$, R$^{8a}$ and R$^{8b}$ are independently
 (a) H,
 (b) C$_1$–C$_8$-alkyl or a substituted C$_1$–C$_8$-alkyl with a COOR$^4$, OCOR$^{4a}$, OH, aryl, or -(CH$_2$)$_{1-4}$R$^4$, -CO-R$^4$, -CO-heteroaryl substituent;
 (c) OR$^{22}$,
 (d) -NO$_2$,
 (e)

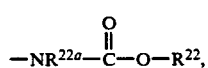

(f) -CONR$^4$R$^{22}$,
 (g)

—NR$^{22a}$—C(=O)—O—R$^{22}$, (h) -NR$^4$R$^{22}$,
 (i) Cl, F, or Br,
 (j) -CF$_3$,
 (k) -CO$_2$R$^4$,
 (l) -CO-aryl,
 (m) -S(O)$_x$-R$^{22}$,
 (n) -SO$_2$-NR$^4$R$^9$,
 (o) -N(R$^{22a}$)SO$_2$R$^{22}$,
 (p) aryl,
 (q) heteroaryl,
 (r) -N(R$^{22a}$)CON(R$^4$)R$^{22}$,
 (s) -N(R$^{22a}$)SO$_2$N(R$^4$)R$^{22}$, or
 (t) -N(R$^{22a}$)SO$_2$OR$^{22}$;
R$^{21}$ is H, F, or Cl;
X is a single bond;
r is one.
3. A compound of claim 2 wherein:
R$^1$ is:
 (a) -SO$_2$N(R$^{22a}$)-OR$^{22a}$,
 (b) -SO$_2$NHSO$_2$R$^{22}$,
 (c)

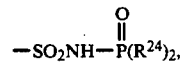

(d) -SO$_2$NHCN,
 (e) -SO$_2$NHCO$_2$R$^{22}$,
 (f)

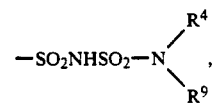

(g) -NHSO$_2$NHSO$_2$R$^{22}$,
 (h)

(i) 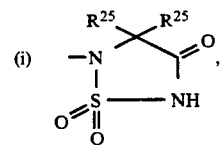

(j) 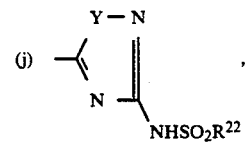

(k) 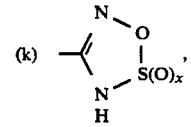

(l) 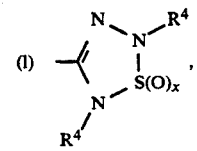

(m) 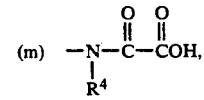

-continued or (n) —NHSO$_2$R$^{22}$;

E is a single bond;

R$^{2b}$ and R$^{3b}$ independently are H, -C$_1$–C$_4$-alkyl, -C$_2$–C$_4$-alkenyl, -C$_2$–C$_4$-alkynyl, -Cl, -F, -CF$_3$;

R$^6$ is -C$_1$–C$_4$-alkyl, -cyclopropyl, -CH$_2$CH$_2$CH$_2$CF$_3$, CH$_2$CH$_2$CF$_3$, -C$_2$–C$_5$-alkenyl, or -cyclopropylmethyl;

R$^{7a}$, R$^{7b}$, R$^{8a}$ and R$^{8b}$ are each independently H, -C$_1$–C$_4$-alkyl, -NO$_2$, -NR$^4$R$^{22}$, -OCH$_3$, -NR$^{22a}$COOR$^{22}$, -Cl, -CH$_2$COOR$^{4a}$, -S(O)$_x$-R$^{22}$, alkyl, NR$^{22a}$CONR$^4$R$^{22}$, CH$_2$OCO(C$_1$–C$_4$-alkyl), NR$^{22a}$COR$^{22}$, -NCOR$^{22}$CO$_2$R$^4$, -F, -CH$_2$Ph, -CONR$^4$R$^{22}$, or CO$_2$R$^4$.

4. A compound of claim 3 of the Formula (II)

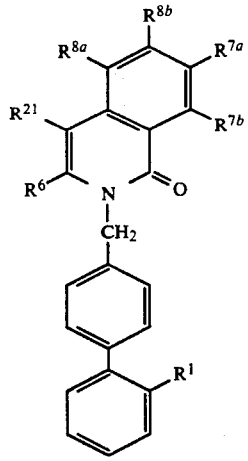

wherein:
R$^4$ is hydrogen or C$_1$–C$_6$-alkyl;
R$^6$ is (a) -C$_1$–C$_4$-alkyl, (b) -CH$_2$CH$_2$CH$_2$CF$_3$, (c) -CH$_2$CH$_2$CF$_3$, (d) cyclopropylmethyl, or (e) cyclopropyl;
R$^{7a}$ is (a) hydrogen, (b) C$_1$–C$_4$-alkyl, (c) -NR$^4$R$^{22}$, (d) -NR$^{22a}$CONR$^4$R$^{22}$, (e) -NR$^{22a}$COR$^{22}$, or (f) -NR$^{22a}$CO$_2$R$^{22}$;
R$^{7b}$ is (a) hydrogen, (b) C$_1$–C$_4$-alkyl, (c) F, or (d) CO$_2$R$^4$;
R$^{8a}$ is (a) hydrogen, (b) C$_1$–C$_4$-alkyl, (c) F;
R$^{8b}$ is (a) hydrogen, (b) C$_1$–C$_4$-alkyl, (c) -CO$_2$R$^4$;
R$^{21}$ is hydrogen or F;
R$^{22}$ is
  (a) phenyl,
  (b) 4-F-phenyl,
  (c) 4-CF$_3$-phenyl, or
  (d) C$_1$–C$_6$-alkyl; and
R$^{22a}$ is
  (a) hydrogen,
  (b) C$_1$–C$_6$-alkyl, or
  (c) benzyl.

5. A pharmaceutical formulation for the treatment of hypertension and congestive heart failure comprising a pharmaceutically acceptable carrier and an effective antihypertensive amount of the compound of claim 1.

6. A method of treating hypertension and congestive heart failure comprising the administration of an effective antihypertensive amount of the compound of claim 1 to a patient in need of such treatment.

* * * * *